(12) United States Patent
Kurosu et al.

(10) Patent No.: US 7,858,825 B2
(45) Date of Patent: Dec. 28, 2010

(54) ACID AND BASE STABLE DIPHENYLMETHANOL DERIVATIVES AND METHODS OF USE

(75) Inventors: Michio Kurosu, Windsor, CO (US); Dean Crick, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 118 days.

(21) Appl. No.: 12/031,833

(22) Filed: Feb. 15, 2008

(65) Prior Publication Data

US 2008/0200719 A1    Aug. 21, 2008

Related U.S. Application Data

(60) Provisional application No. 60/901,926, filed on Feb. 15, 2007.

(51) Int. Cl.
*C09B 11/02* (2006.01)
*C40B 80/00* (2006.01)
*C07C 69/76* (2006.01)
*C07C 43/20* (2006.01)

(52) U.S. Cl. .............. 564/315; 564/323; 564/326; 506/42; 560/57; 560/159; 560/129; 568/649

(58) Field of Classification Search ........... 560/57, 560/129, 159; 564/315, 323, 326; 568/649, 568/772; 506/42; 556/413; 525/342
See application file for complete search history.

(56) References Cited

U.S. PATENT DOCUMENTS

| 4,508,926 A | * | 4/1985 | Toth et al. .................. 568/766 |
| 4,564,630 A | * | 1/1986 | Toth et al. .................. 514/478 |
| 4,605,672 A | * | 8/1986 | Toth et al. .................. 514/648 |
| 4,605,785 A | * | 8/1986 | Toth et al. .................. 568/649 |
| 4,618,611 A | * | 10/1986 | Toth et al. ............. 514/252.12 |
| 4,645,779 A | * | 2/1987 | Toth et al. .................. 514/648 |

OTHER PUBLICATIONS

Lyttle et al., A new universal inker for solid phase DNA synthesis, 1996, Nucleic Acids Research, nol. 24, No. 14, pp. 2793-2798.*
Bunin, B., The Combinatorial Index, Chapter 3 Linkers for Solid-Phase Synthesis, 1998, Academic Press, (abstract pages 12).*
Eggenweiler, Linkers for solid-phase synthesis of small molecules: coupling and cleavage techniques, 1998, Drug, Discoveris & Therapeutics, vol. 3, No. 12, (8 pages).*

* cited by examiner

*Primary Examiner*—Porfirio Nazario Gonzalez
*Assistant Examiner*—Yate' K Cutliff
(74) *Attorney, Agent, or Firm*—Don D. Cha; Hamilton DeSanctis & Cha, LLP

(57) ABSTRACT

The invention provides compounds that are useful as linkers for solid phase synthesis and as protecting groups, and methods for producing and using the same.

25 Claims, No Drawings

ACID AND BASE STABLE DIPHENYLMETHANOL DERIVATIVES AND METHODS OF USE

CROSS-REFERENCE TO RELATED APPLICATIONS

This application claims the priority benefit of U.S. Provisional Application No. 60/901,926, filed Feb. 15, 2007, which is incorporated herein by reference in its entirety.

STATEMENT REGARDING FEDERALLY FUNDED RESEARCH

The U.S. Government has a paid-up license in this invention and the right in limited circumstances to require the patent owner to license others on reasonable terms as provided for by the terms of Grant Nos. AI049151 and AI065357 awarded by the National Institutes of Health.

FIELD OF THE INVENTION

The invention relates to compounds that are useful as linkers for solid phase synthesis and as protecting groups, and methods for producing and using the same.

BACKGROUND OF THE INVENTION

Carboxylic acid functional groups are present in a wide variety of compounds including amino acids, pharmaceutically active compounds, polymers, etc. Carboxylic acids are also used in many solid-phase synthesis to form esters, amides, and other carbonyl linkages. In addition, carboxylic acid functional groups are used to form a wide variety of different functional groups. However, in many instances when a carboxylic acid functional group is present in the molecule, it can interfere with other desired reactions. In these instances, the carboxylic acid group is protected to avoid undesired side reactions.

While there are a variety of protecting groups available for carboxylic acids, each has different reactivity and use. In many instances, it is desirable to be able to remove the carboxylic acid protecting group selectively or simultaneously in the presence of other functional group protecting groups. This is especially true in syntheses of target molecules that require multiple different protecting groups. If one can remove several protecting groups in a single reaction, it would reduce the time and cost of synthesis of target compound.

The widely utilized protecting groups for alcohol (e.g., diol) compounds are cleavable ether or silyl ethers or esters via acidic or basic conditions. Acetal is a typical protecting group for carbonyl molecules. Carboxylic acids are generally protected as their esters or orthoesters. There are many instances in organic synthesis where simultaneous or "one-pot" removal of protecting groups is needed or desired. Unfortunately, there are limitations of available carboxylic acid protecting groups and/or deprotection conditions that allow such one-pot removal of carboxylic acid protecting group with other protecting groups for alcohols or amines or carbonyls.

Therefore, there is a need for novel protecting groups which can be used in a variety of applications, including carboxylic acid protecting groups, linkers for solid-phase organic synthesis, etc., that can react with carboxylic acid functional group and allow for removal under a relatively mild conditions.

SUMMARY OF THE INVENTION

Some aspects of the invention provide a compound of the formula:

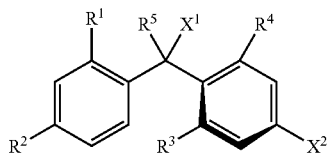

I where
each of $R^1$, $R^2$, $R^3$, and $R^4$ is independently hydrogen, lower alkyl, or halide, provided at least one of $R^1$, $R^2$, $R^3$, and $R^4$ is halide;
$R^5$ is hydrogen or alkyl;
each of $X^1$ and $X^2$ is independently —$OR^6$, —$NR^7R^8$, or —$SR^9$;
each $R^6$ is independently hydrogen, alkyl, carbonyl, or a hydroxy protecting group;
each $R^7$ is independently hydrogen or alkyl;
each $R^8$ is independently hydrogen, alkyl, or a nitrogen protecting group; and
each $R^9$ is independently hydrogen, alkyl, or a thiol protecting group.

and solid-substrate comprising the same.

Other aspects of the invention provide solid-supports comprising a compound of Formula I, and methods for using the same in, for example, solid-phase synthesis and combinatorial library synthesis.

Compounds of the invention can also be used as protecting group for a variety of functional groups including, but not limited to, carboxylic acids, hydrazines, etc.

DETAILED DESCRIPTION OF THE INVENTION

"Alkyl" refers to a saturated linear monovalent hydrocarbon moiety of one to twenty, typically one to twelve, carbon atoms or a saturated branched monovalent hydrocarbon moiety of three to twenty, typically three to twelve, carbon atoms. Exemplary alkyl group include, but are not limited to, methyl, ethyl, n-propyl, 2-propyl, tert-butyl, pentyl, and the like.

"Alkylene" refers to a saturated linear saturated divalent hydrocarbon moiety of one to twenty, typically one to twelve, carbon atoms or a branched saturated divalent hydrocarbon moiety of three to twenty, typically three to twelve, carbon atoms. Exemplary alkylene groups include, but are not limited to, methylene, ethylene, propylene, butylene, pentylene, and the like.

"Aryl" refers to a monovalent mono-, bi- or tricyclic aromatic hydrocarbon moiety of 6 to 15 ring atoms which is optionally substituted with one or more, typically one, two, or three substituents within the ring structure. When two or more substituents are present in an aryl group, each substituent is independently selected. Often aryl is phenyl.

The terms "halo," "halogen" and "halide" are used interchangeably herein and refer to fluoro, chloro, bromo, or iodo.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its mirror image.

"Enantiomeric excess" refers to the difference between the amount of enantiomers. The percentage of enantiomeric excess (% ee) can be calculated by subtracting the percentage of one enantiomer from the percentage of the other enantiomer. For example, if the % ee of (R)-enantiomer is 99% and % ee of (S)-enantiomer is 1%, the % ee of (R)-isomer is 99%-1% or 98%.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any narrow and/or preferred, more preferred and most preferred definitions, if any.

Some aspects of the invention provide a compound of the formula:

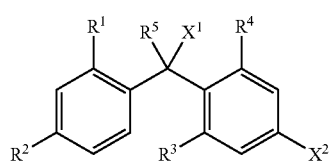

I where
each of $R^1$, $R^2$, $R^3$, and $R^4$ is independently hydrogen, lower alkyl, or halide, provided at least one of $R^1$, $R^2$, $R^3$, and $R^4$ is halide;
$R^5$ is hydrogen or alkyl;
each of $X^1$ and $X^2$ is independently —$OR^6$, —$NR^7R^8$, or —$SR^9$;
each $R^6$ is independently hydrogen, alkyl, carbonyl, or a hydroxy protecting group;
each $R^7$ is independently hydrogen or alkyl;
each $R^8$ is independently hydrogen, alkyl, or a nitrogen protecting group; and
each $R^9$ is independently hydrogen, alkyl, or a thiol protecting group.

It should be appreciated that since compounds of Formula I have a chiral center between the two aryl groups, compounds of the invention can exist as a racemate (i.e., racemic mixture), enantiomerically enriched mixture, or enantiomerically pure compounds. Accordingly, the scope of the invention includes a racemate, enantiomerically enriched mixture and enantiomerically pure compounds of Formula I.

In some embodiments, at least two of $R^1$, $R^2$, $R^3$, and $R^4$ are halides. In other embodiments, at least three of $R^1$, $R^2$, $R^3$, and $R^4$ are halides. Still in other embodiments, $R^1$, $R^2$, $R^3$, and $R^4$ are halides.

Yet in other embodiments, each halide is independently selected from the group consisting of Cl, Br, and I. Within these embodiments, in some instances halide is Cl.

Still in other embodiments, $R^5$ is hydrogen.

In other embodiments, $X^1$ is —$OR^6$, where $R^6$ is as defined herein. In some instances within these embodiments, $R^6$ is hydrogen or carbonyl.

Yet still in other embodiments, $X^2$ is —$OR^6$, where $R^6$ is as defined herein. Within these embodiments, in some instances $R^6$ is alkyl.

Other aspects of the invention provide solid-substrate comprising the compound of Formula I. Some particular aspects of the invention provide a solid-substrate of the formula:

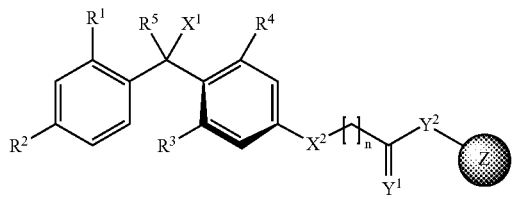

where
n is an integer from 1 to about 20;
each of $R^1$, $R^2$, $R^3$, and $R^4$ is independently hydrogen, lower alkyl, or halide, provided at least one of $R^1$, $R^2$, $R^3$, and $R^4$ is halide;
$R^5$ is hydrogen or alkyl;
X is —$OR^6$, —$NR^7R^8$, or —$SR^9$;
each of $X^2$ and $Y^2$ is independently —O—, —$NR^8$—, or —S—;
$R^6$ is hydrogen, alkyl, carbonyl, or a hydroxy protecting group;
$R^7$ is hydrogen or alkyl;
each $R^8$ is independently hydrogen, alkyl, or a nitrogen protecting group;
$R^9$ is hydrogen, alkyl, or a thiol protecting group;
$Y^1$ is O, $NR^{10}$, or S;
$R^{10}$ is hydrogen, alkyl, —$OR^{11}$, or —$NR^{12}$;

$R^{11}$ and $R^{12}$ are hydrogen or alkyl; and

Z is a solid substrate.

In some embodiments, $R^1$, $R^2$, $R^3$, and $R^4$ are halides. Within these embodiments, in some instances each halide is independently selected from the group consisting of Cl, Br, and I. In other instances, halide is Cl.

Still in other embodiments, $R^5$ is hydrogen.

Yet in other embodiments, $X^1$ is —$OR^6$, where $R^6$ is that defined herein. Within these embodiments, in some instances $R^6$ is hydrogen or carbonyl.

In other embodiments, $X^2$ is —O—.

Still yet in other embodiments, $Y^1$ is O.

Yet in other embodiments, $Y^2$ is —$NR^8$—, where $R^8$ is as defined herein.

Still yet in other aspects, methods for performing solid-phase synthesis are provided. Such methods typically comprise:

(a) contacting a solid-substrate of the formula:

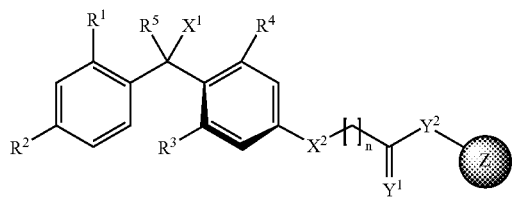

with a first reactive reagent comprising a first corresponding functional group chemically reactive with $X^1$ of the solid-substrate under conditions sufficient to react the corresponding functional group with $X^1$, thus providing a solid-substrate bound product;

(b) optionally reacting the solid-substrate bound product and another reactive reagent comprising another corresponding functional group under conditions sufficient to produce a growing polymeric chain; and (c) repeating said step (b) until a desired product is obtained, where n is an integer from 1 to about 20;

each of $R^1$, $R^2$, $R^3$, and $R^4$ is independently hydrogen, lower alkyl, or halide, provided at least one of $R^1$, $R^2$, $R^3$, and $R^4$ is halide;

$R^5$ is hydrogen or alkyl;

$X^1$ is —OH, —$NHR^8$, or —SH;

each of $X^2$ and $Y^2$ is independently —O—, —$NR^8$—, or —S—;

each $R^8$ is independently hydrogen, alkyl, or a nitrogen protecting group;

$Y^1$ is O, $NR^{10}$, or S;

$R^{10}$ is hydrogen, alkyl, —$OR^{11}$, or —$NR^{12}$;

$R^{11}$ and $R^{12}$ are hydrogen or alkyl; and

Z is a solid substrate.

In some embodiments, the reactive reagent is selected from the group consisting of a nucleotide, saccharide, amino acid, and a derivative thereof. In this manner, oligonucleotides, polysaccharides, oligopeptides, and various small molecules can be prepared using methods, compounds, and linker of the invention.

In some embodiments, Z is a bead, wafer, film, disc or plate. In some instances within these embodiments, Z comprises a material selected from organosilane-treated glass, organosilane-treated silicon, polypropylene, polyethylene, and polystyrene.

Yet other embodiments of the invention provide a method for producing a compound of the formula:

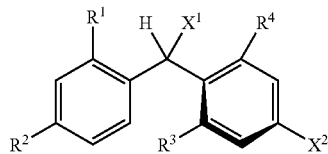

said method comprising:

contacting an acyl halide compound of the formula:

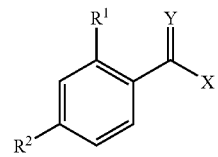

with an aromatic compound of the formula:

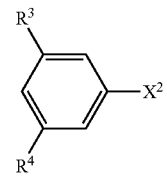

in the presence of a coupling catalyst under conditions sufficient to produce the compound of Formula IA, where each of $R^1$, $R^2$, $R^3$, and $R^4$ is independently hydrogen, lower alkyl, or halide, provided at least one of $R^1$, $R^2$, $R^3$, and $R^4$ is halide;

each of $X^1$ and $X^2$ is independently —$OR^6$, —$NR^7R^8$, or —$SR^9$;

each $R^6$ is independently hydrogen, alkyl, carbonyl, or a hydroxy protecting group;

each $R^7$ is independently hydrogen or alkyl;

each $R^8$ is independently hydrogen, alkyl, or a nitrogen protecting group; and each $R^9$ is independently hydrogen, alkyl, or a thiol protecting group.

It is to be understood that the scope of this invention encompasses not only the various isomers which may exist but also the various mixture of isomers which may be formed.

Combination of various embodiments can form other embodiments. For example, in some embodiments, $R^1$, $R^2$, $R^3$, and $R^4$ are halide, and halide is chloride. Thus, in this combination of embodiments, $R^1$, $R^2$, $R^3$, and $R^4$ are chloride. In this manner, a wide range of embodiments are encompassed within the scope of the invention.

If the compound of the present invention contains one or more chiral centers, the compound can be synthesized enantioselectively or a mixture of enantiomers and/or diastereomers can be prepared and separated. The resolution of the compounds of the invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety results in forms that are separable by fractional crystallization, distillation or chromatography.

As stated above, the racemic compounds of Formula I can be resolved or separated (i.e., enantiomerically enriched) using any of the variety of chiral resolution methods known to one skilled in the art. Such resolution methods are described, for example, in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety.

In some resolution methods, a racemic mixture is converted to a mixture of diasteromers by attachment, either chemically or enzymatically, of a relatively enantiomerically pure moiety. Unlike enantiomers, most diastereomers have different physical properties, e.g., solubility, boiling point, affinity (e.g., to chromatography columns and enzymes), and the like. These different physical properties can be used to separate one diastereoisomer from another, for example, by fractional crystallization, distillation, chromatography, kinetic resolution using an enzyme, and the like.

Compounds of the invention can be prepared from readily available starting materials using the methods and procedures described herein or known to one skilled in the art. Various substituents on the compounds of the invention can be present in the starting compounds, added to any one of the intermediates or added after formation of the final products by known methods of substitution or conversion reactions. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, 3$^{rd}$ ed., John Wiley & Sons, New York, 1999, and references cited therein, all of which are incorporated herein by reference in their entirety.

Although a particular aspect of the invention is illustrated in the schemes below, those skilled in the art will recognize that all aspects of the invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Since the compounds of the present invention can have certain substituents that may be present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art.

Utility

Protecting Group

Compounds of the invention can be used as a protecting group for the carboxylic acid. When used in such a manner, compounds of the invention can be cleaved simultaneously or in one-pot with the acetonide by a volatile and mild acid such as trifluoroacetic acid (TFA). In some embodiments, compounds of the invention as protecting groups for the carboxylic acid have stability to relatively strong Brønsted and Lewis acids, bases, and a wide variety of nucleophiles. Although a large number of acid cleavable protecting groups (i.e., trityl, TBDPS, methoxymethyl, tetrahydropyranyl, 2-(trimethylsilyl)ethyl, t-butyl, p-methoxybenzyl, ortho esters, and their related protecting groups) for carboxylic acids have been utilized in organic syntheses, these protecting groups did not fulfill the stability against conditions being utilized in the library productions; trityl, silyl, and MPM protecting groups are too labile to acids, and MOM, SEM, t-butyl, and ortho esters require harsh acidic conditions for the regeneration of the carboxylic acids. In contrast, compounds of the invention can be used as a protecting group for carboxylic acids and is stable to acids and bases, and a wide variety of nucleophiles. Moreover, in some instances compounds of the invention can be regenerated by TFA.

Solid-phase Synthesis/Combinatorial Library

Since introduction of the concept of solid-phase synthesis in the late 1950's, a variety of linkers for immobilizing organic molecules and organic reactions amenable to polymer-supported chemistries have been developed, greatly advancing research in biochemistry, molecular biology, pharmacology, drug discovery, organic chemistry, and other fields. Although recent advances in analysis and purification methods significantly enhanced the usefulness of solid-phase synthesis, development of new linker which allows delivering target molecules in high yield and purity is still required. Ideally, the linkers should be stable against a planned set of reaction conditions, but be cleaved under mild conditions that do not degrade the products. To date, many useful linkers for solid-phase synthesis have been developed. However, the choice of spacer and linker requires careful consideration when applying diverse organic reactions on the solid phase.

Compounds of the invention can also be used as a linker in solid-phase synthesis. Accordingly, some aspects of the invention provide a solid-substrate of the formula:

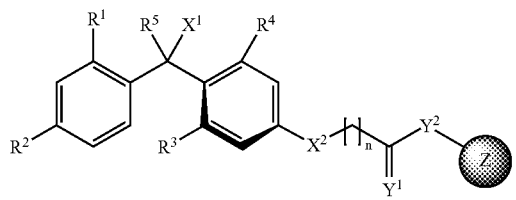

where
- n is an integer from 1 to about 20;
- each of $R^1$, $R^2$, $R^3$, and $R^4$ is independently hydrogen, lower alkyl, or halide, provided at least one of $R^1$, $R^2$, $R^3$, and $R^4$ is halide;
- $R^5$ is hydrogen or alkyl;
- $X^1$ is —OR, —$NR^7R^1$, or —$SR^9$;
- each of $X^2$ and $Y^2$ is independently —O—, —$NR^8$—, or —S—;
- $R^6$ is hydrogen, alkyl, carbonyl, or a hydroxy protecting group;
- $R^7$ is hydrogen or alkyl;
- each $R^8$ is independently hydrogen, alkyl, or a nitrogen protecting group;
- $R^9$ is hydrogen, alkyl, or a thiol protecting group;
- $Y^1$ is O, $NR^{10}$, or S;
- $R^{10}$ is hydrogen, alkyl, —$OR^{11}$, or —$NR^{12}$;
- $R^{11}$ and $R^{12}$ are hydrogen or alkyl; and
- Z is a solid substrate.

Typically, $X^1$ is used as a function group for linking other compound(s) in solid-phase synthesis. In some embodiments, $X^1$ is —OH. In these embodiments, solid-substrate of Formula II can be used as a linker for various functional groups including, but not limited to, carboxylic acids, amines, alcohols, and phenols. It has been found by the present inventors that solid-substrate of Formula II are stable to Brønsted and Lewis acids, Brønsted bases and a wide variety of nucleophiles. However, solid-substrate of Formula II can conveniently be cleaved, e.g., by the solvolytic displacement reactions with a mild acid, such as 20% TFA.

Schematic illustrations for using solid-substrate of Formula II is shown below:

As can be seen in Scheme I, a wide variety of compounds can be prepared, e.g., carboxylic acids, amines, alcohols, phenols, etc. Compounds can be released from the solid-substrate by mild acid treatment, e.g., TFA solvolysis. In Scheme I, $R^1$-$R^4$ are those defined herein. Often $R^1$-$R^4$ are halides. More often $R^1$-$R^4$ are chloro.

In addition to solid-phase synthesis, compounds and solid-substrates of the invention can be used in preparation of a variety of library of compounds. For example, Scheme II below illustrates using solid-substrate of Formula II for preparing a combinatorial library of MraY inhibitors based on uridine-β-hydroxyamino acid.

Scheme II. General structures of MraY inhibitors i.

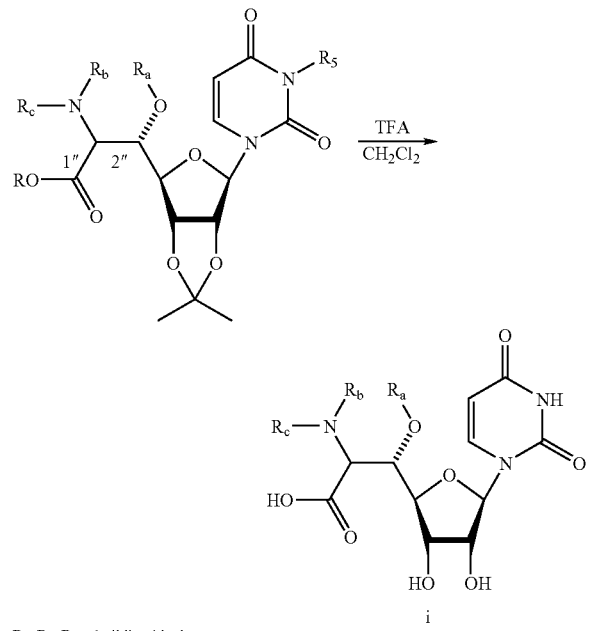

$R_a$, $R_b$, $R_c$ = building blocks
R = acid-cleavable protecting group (Solid-support of Formula II)
$R_d$ = BOM or H

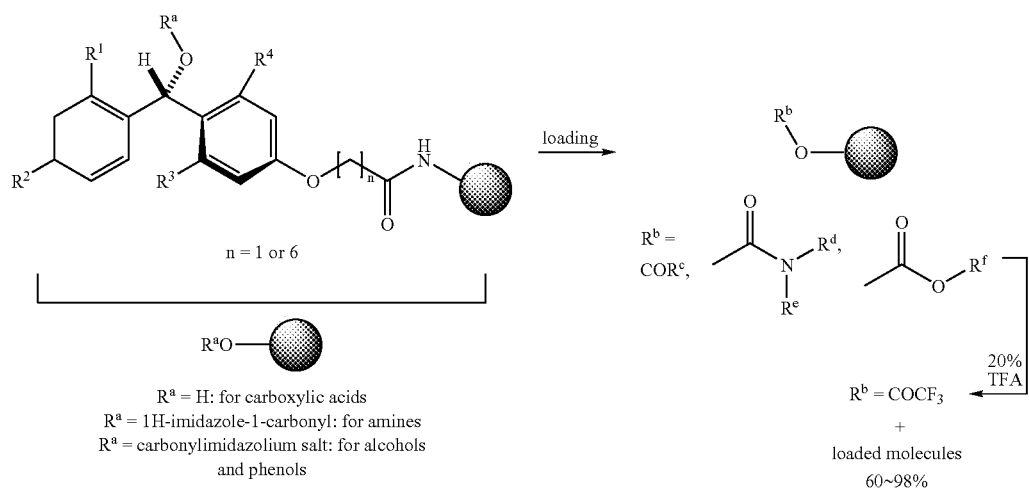

In Scheme II, R—O— moiety corresponds to solid-substrate of Formula II where $X^1$ is O of R—O—. Diphenylmethyl ester is an acid labile functional group and has been utilized as a temporary protecting group for carboxylic acids. Typically, diphenylmethanol exhibits similar nucleophilicity to allylic alcohol and is not esterified efficiently with carboxylic acids via conventional carboxylic acid activation methods (e.g., DCC, BOPCl, and mixed anhydride). In order to stabilize diphenylmethyl esters by changing the electronic properties of dibenzene moieties, several halide substituted-diphenylmethyl esters were prepared and evaluated for stability against various acids such as $TsOH.H_2O$ (20% in $CH_2Cl_2$-THF), HF (10% in $CH_3CN$), $BF_3.OEt_2$ (10% in $CH_2Cl_2$), and $La(OTf)_3$ (10% in aq THF). As summarized in Scheme III, (4-methoxyphenyl)(halophenyl)methanols 4a-d were efficiently esterified by using EDCI, DCC or acid chloride methods. The esters 4a-c regenerated the corresponding acids by the treatment of 20% TsOH within 1 h and were also not stable under 10% HF, 15% TFA, 10% $BF_3.OEt_2$, and 10% $La(OTf)_3$. The esters 4a-d were synthesized by Friedel-Crafts reactions followed by reduction of the carbonyl group, for example, using a reducing group such as $NaBH_4$.

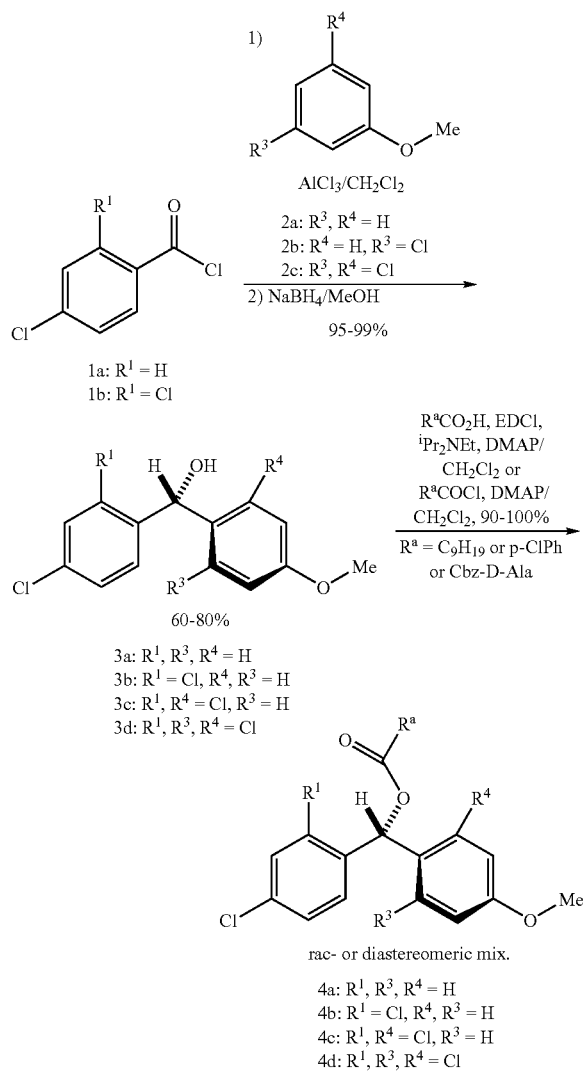

| entry | TsOH[a] | HF[b] | TFA[c] | $BF_3 \cdot OEt_2$[d] | $La(OTf)_3$[d] |
|---|---|---|---|---|---|
| 4a | H | H | H | H | H |
| 4b | H | H | H | H | H |
| 4c | H | H | H | H | H |
| 4d | L | L | L | Me | L |

[a] 20% in $CH_2Cl_2$-THF (1/1).;
[b] 10% in $CH_3CN$.;
[c] 15% in $CH_2Cl_2$.;
[d] 10% in aq THF.; H indicates the protecting group is readily cleaved.; M indicates that the protecting group is cleaved very slowly.; L indicates that the protecting group is stable.;
[e] ~5% of regeneration of the carboxylic acids was observed after 1 h.

The tetrachloro-substituted 4-methoxydiphenylmethyl esters 4d are stable to various acidic conditions, for example, no regeneration of the acids from the esters 4d were observed under 20% TsOH for over 20 h. The esters 4d were also stable to 15% TFA, 10% HF, and a variety of Lewis acids such as $AlCl_3$, $B(C_6F_5)_3$, $BCl_3$, TMSOTf, and $La(OTf)_3$. Moreover, the esters 4d were (1) photolytically stable, e.g., no change by the irradiation at 200~350 nm in DMF for 72 h; (2) showed stability under basic conditions, e.g., no saponifications were observed under 40% $NH_4OH$ in aq THF, 10% LiOH in aq THF-MeOH, 10% KOH in MeOH-THF, and 10% DBU in aq THF at rt for over 12 h; and (3) showed excellent stability to nucleophiles, e.g., the esters 4d were not susceptible to the nucleophilic attacks of primary or secondary amines (in aqueous THF at 80° C.), $NH_2NH_2$ (in aq THF at rt), alkylthiols (in THF at 80° C.), and $NaN_3$ (90° C. in DMF) for over 12 h.

In some instances, the esters 4d slowly reacted with 10% $BF_3.OEt_2$ to furnish the carboxylic acids (~5% after 1 h) and 1,3-dichloro-2-((2,4-dichlorophenyl)fluoromethyl)-5-methoxybenzene. The esters 4d could conveniently be cleaved by using 20% TFA in $CH_2Cl_2$ to afford the corresponding acids and the trifluoroacetate ($R^1$, $R^3$, and $R^4$=Cl, $R_a$=$CF_3$ in 4d). Thus, compounds of the invention enabled a wide range of organic reactions for the generation of libraries of MraY inhibitors in solution (Scheme III). Compounds of the invention, e.g., (2,6-dicholoro-4-methoxyphenyl)(2,4-dichlorophenyl)methanol, can also be used as linkers to immobilize carboxylic acids, amines, alcohols, as well as other functional groups which can, however, be cleaved by 20% TFA.

As illustrated in Scheme IV below, the 3,5-dichloro-4-((2,4-dichlorophenyl)-(hydroxy)methyl)phenol group could be linked with (aminomethyl)polystyrene 7a and aminomethyl-Lantern™ 7b through spacers (e.g., $C_2$-$C_7$ spacers). Available alcohol-linkers on the polymer surface after derivatization of the polymers 7a (~1.2 mmol/g) and 7b (~15 μmol/Lantern) were determined to be 1.0~1.2 mmol/g for 8a-$C_2$ and 8a-$C_7$, and 12~15 μmol/Lantern for 8b-$C_2$ and 8b-$C_7$ by coupling of the linkers with Fmoc-β-Ala-OH and subsequent release of Fmoc chromophore and elemental analyses of the chlorine atoms for 8a and 8b.

Scheme IV. Synthesis of the hydroxy-tetrachlorodiphenylmethyl (HTPM) linkers.

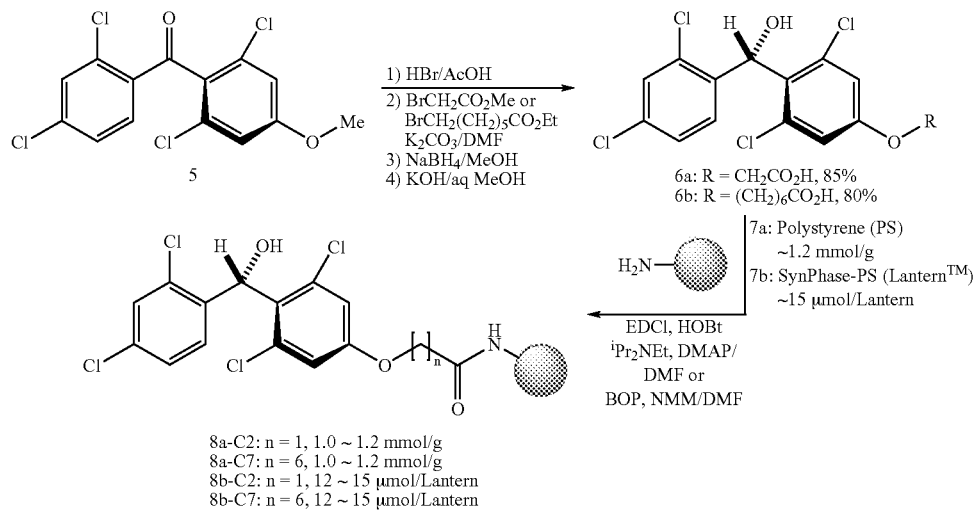

8a-C2: n = 1, 1.0 ~ 1.2 mmol/g
8a-C7: n = 6, 1.0 ~ 1.2 mmol/g
8b-C2: n = 1, 12 ~ 15 μmol/Lantern
8b-C7: n = 6, 12 ~ 15 μmol/Lantern No significant noticeable differences in the rates of esterification with N-blocked amino acids between 8a-C2 and 8a-C7 or between 8b-C2 and 8b-C7 were observed; a variety of Cbz or Boc-protected amino acids could be loaded onto 8a-C2, 8a-C7, 8b-C2, and 8b-C7 within 6 h in >95% yields using a 4~5 fold excess of N-protected amino acids and EDCI or DICI. In general, Cbz-D-alanyl esters of 8a-C2 and 8b-C2 showed excellent stability to $BF_3 \cdot OEt_2$; on the other hand, ~10% of the same esters of 8a-C7 and 8b-C7 were cleaved after 2 h. Robustness of the linkers 8a-C2 and 8b-C2 to an acid (20% TsOH) was demonstrated by synthesizing the pentapeptide moiety of Park's nucleotide (UDP-N-acetylmuramyl-L-alanyl-D-isoglutamyl-L-lysinyl-D-alanyl-D-alanine) using the Boc-strategy. One gram of the Boc-D-Ala-HTPM resin (~1.0 mmol/g) was used for the following sequential ligation reactions with Boc-D-Ala-OH, Boc-L-Lys($COCF_3$)-OH, Boc-γ-D-Glu(OMe)-OH, Cbz-L-Ala-OH. The generated pentapeptide on the HTPM resin was cleaved with 20% TFA in $CH_2Cl_2$ for 1 h followed by methylation with $CH_2N_2$ to afford Cbz-L-Ala-γ-D-Glu(OMe)-L-Lys($COCF_3$)-D-Ala-D-Ala-OMe in over 90% overall yield after $SiO_2$-plug filtration ($CHCl_3$:MeOH=3:1). As observed in the esters 4d, 8a-C2 could be regenerated by ammonolysis of the recovered resins and the regenerated HTPM linker was reused two times for the synthesis of Cbz-L-Ala-γ-D-Glu(OMe)-L-Lys($COCF_3$)-D-Ala-D-Ala-OMe; the overall yields using the regenerated resins were 90% (1$^{st}$ reuse) and 89% (2$^{nd}$ reuse), respectively.

Scheme V. [a] A demonstration of loading onto and cleavage from the HTPM-resin using the carboxylic acid 9.

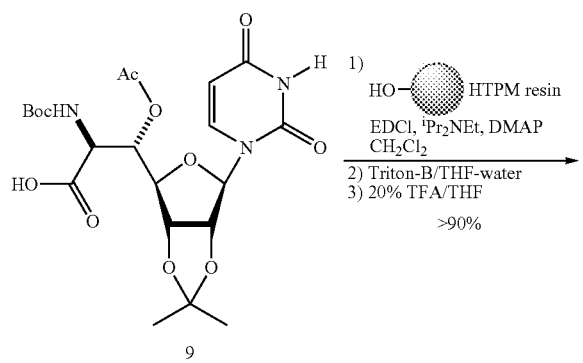

-continued

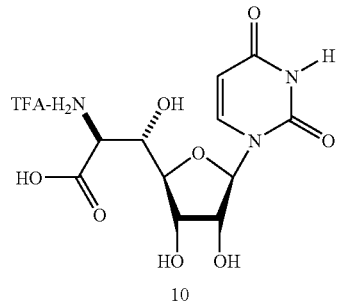

Solid phase peptide synthesis has proven to be a practical method of producing synthetic oligo-peptides and the use of Boc-protecting group (Boc-solid phase synthesis) is a popular method currently used for oligo peptide synthesis. However, the Boc-solid phase peptide synthesis suffers from low overall yield and low purity due to (1) partial cleavage of the anchor peptides in the cycle of the deprotection of Boc groups, and (2) inefficient cleavage of the products when applied to photolabile linkers. In contrast, synthesis of the oligopeptide using the HTPM linker 8a-C2 provided excellent yield and purity. As shown in Scheme V, uridine-β-hydroxyamino acid compound 9 was linked to a solid phase using 1.3 eq of the HTMP resin 8a-C2. The ester linker was stable to the basic conditions such as Triton B and/or $NH_4OH$ in aq THF-MeOH. The acetonide deprotection and concomitant cleavage of the linker under 20% TFA provided the fully deprotected uridine-β-hydroxyamino acid 10 in over 90% (Scheme V).

The HTPM linker 8a-C2 was converted to the carbonylimidazole linker 8a-C2-CI by the reaction with CDI, which was further converted to the carbonylimidazolium salts 8a-C2-CI-Me by the treatment with MeI in $CH_3CN$ or MeOTf in $CH_2Cl_2$. The resin 8a-C2-CI exhibited excellent reactivity against primary and secondary amines but much less reactivity towards alcohol nucleophiles; the primary alcohols appeared to not react with the carbonylimidazole resin even in the presence of tertiary amines at elevated temperatures.

Thus, the resin 8a-C2-CI was selectively loaded with amino groups in the presence of alcohol groups in the same molecule.

In contrast, the corresponding carbonylimidazolium salts 8a-C2-CI-Me was utilized in the immobilization of alcohols and phenols in the presence of DMAP in CH$_2$Cl$_2$ at rt. Difference in the loading efficiency of 8a-C2-CI-Me due to the difference of the counter ion (I vs OTf) was not observed. As illustrated in Scheme VI benzylamine (11), N-methylbenzylamine (12), 2-aminopropan-1-ol (13), (2-methoxyphenyl)hydrazine (14) were successfully loaded onto and cleaved from the 8a-C2-CI linker. The overall yields for two steps were over 98%. 3-Phenylpropan-1-ol (15), 4-phenylbutan-2-ol (16), the partially protected uridine 17, (4-chlorophenyl)(4-hydroxyphenyl)methanone (18), and estrone (19) were also loaded onto and cleaved from 8a-C2-CI-Me in 60~70% yield. 3-Formylrifamycin (20) was loaded almost completely using an excess of 8a-C2-CI-Me. A useful level of loading of alcohols and phenols onto the 8a-C2-CI-Me was also achieved. The carbamate and the carbonate linkers exhibited excellent stability to acids, bases, and a variety of nucleophiles as demonstrated for the esters 4d.

Some aspects of the invention provide acid and base stable linkers (e.g., hydroxy-tetrachlorodiphenylmethyl, or HTPM). Linkers of the invention have significant advantages over currently utilized linkers for loading carboxylic acids, for example, (1) the ester linker is stable to a wide variety of nucleophiles, (2) the loaded molecules can be cleaved by solvolytic cleavage with 20% TFA within 1 h, and (3) the linker can be regenerated by treatment with aq NH$_3$ in THF. Linkers of the invention are useful in loading a wide variety of functional groups including, but not limited to, amines, alcohols, and phenols, for example using a carbonylating reagent. Linkers of the invention can be used in polymer-supported organic synthesis. Linkers of the invention can be used to generate diverse structures of libraries.

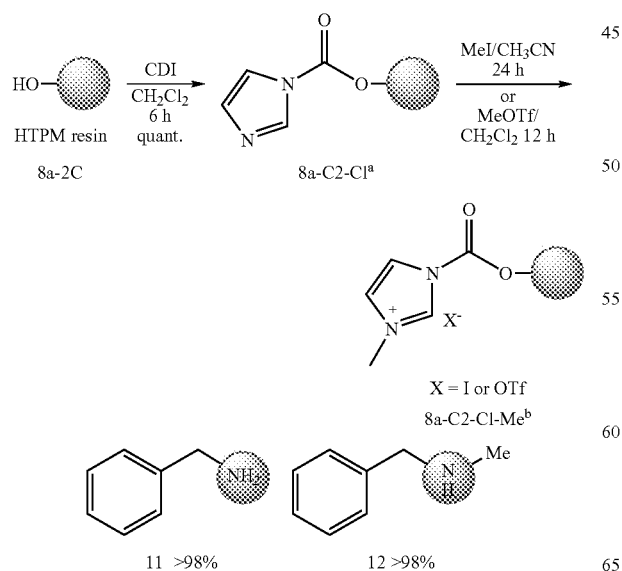

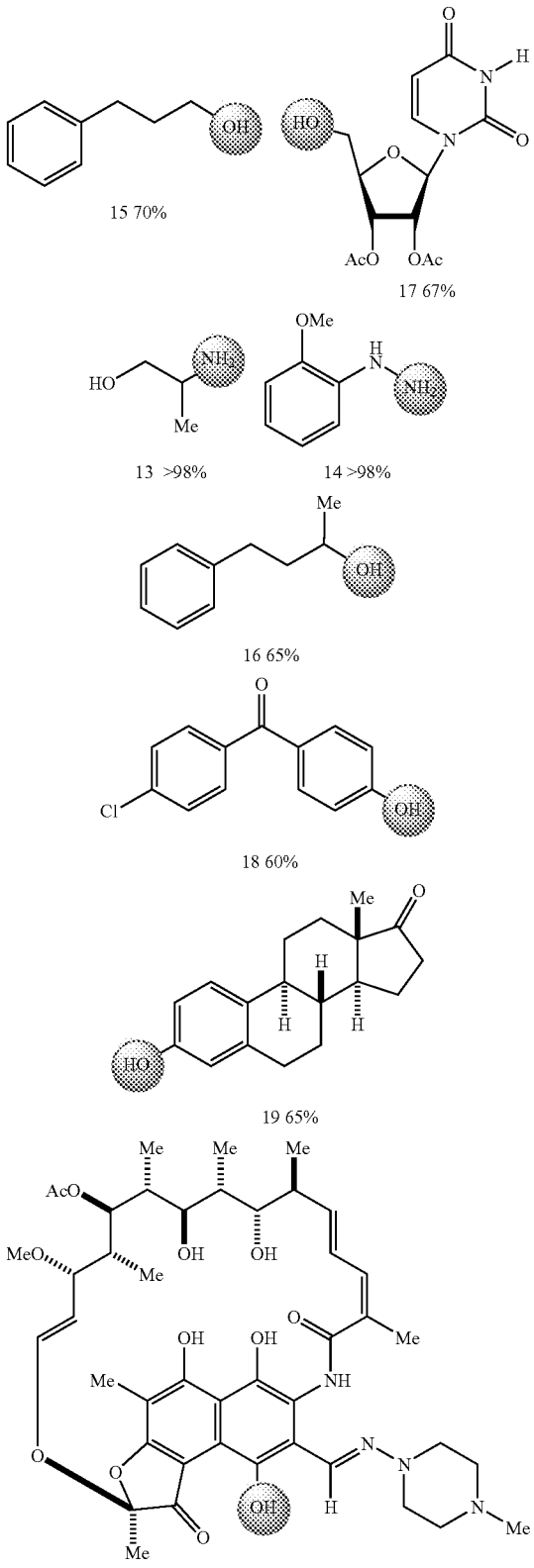

a. 5 equiv of the amine was used in CH$_2$Cl$_2$.
b. 5 equiv of the alcohol and DMAP were used in CH$_2$Cl$_2$.
c. 2 equiv of the resin was used.

Additional objects, advantages, and novel features of this invention will become apparent to those skilled in the art upon examination of the following additional examples thereof, which are not intended to be limiting.

EXAMPLES

Example 1

Synthesis of Uridine-Amino Alcohol-Based Small Optimized Libraries

*Mycobacterium tuberculosis* (Mtb) causes tuberculosis (TB) and is responsible for nearly two million deaths annually. Currently, about 42 million people are HIV-infected and almost one-third are also infected with Mtb. Persons infected with both HIV and Mtb are 30 times more likely to progress to active TB disease. Recent studies have shown that infection with Mtb enhances replication of HIV and may accelerate the progression of HIV infection to AIDS. The current recommended approach to TB treatment is the local directly observed treatment strategy (DOTS). Even where DOTS has been established, if the multidrug-resistant (MDR) rate locally is high, first line drugs (isoniazid, rifampicin, pyrazinamide, and ethambutol) alone give an unacceptably low cure rate. Moreover, if the patient remains ill the transmission rate is increased. Clinical responses of MDR-TB patient to first line drug have been poor, and in some cases there is no response at all. Second line drugs (amikacin, cycloser-ine, ethionimide, kanamycin, capreomycin, and ofloxacin) are often poorly effective and tolerated.

Several promising TB drug leads such as diarylquinoline, fluoroquinolone, and nitroimidazole have been developed based upon known templates. Because of high rate of failure of promising drug leads in rate clinical trials, it is desirable to increase the number of pipeline TB drug leads which affect different drug targets.

Ribosamino-uridine-containing compounds inhibit MraY enzyme of *Mycobacterium tuberculosis*, show antibacterial activity in vitro, and show good in vivo activity in mice models when administered intravenously. Unfortunately, high hydrophilicity nature of current ribosamino-uridine-containing MraY inhibitors results in significantly poor pharmacokinetics. Thus, fine tuning of physico-chemical properties is needed to improve biological activity. In addition, for TB therapy it is desirable to improve properties of oral absorption and high distribution to lung tissues.

Without being bound by any theory, it is believed that the uridine moiety in MraY inhibitors of natural product origin place a significant role in biological activities. One method of using compounds and/or solid-substrates of the invention is illustrated Scheme A below for synthesis of MraY inhibitors.

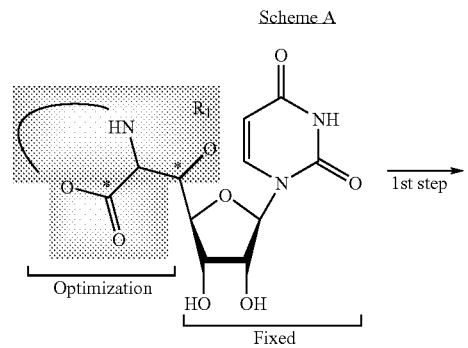

Scheme A

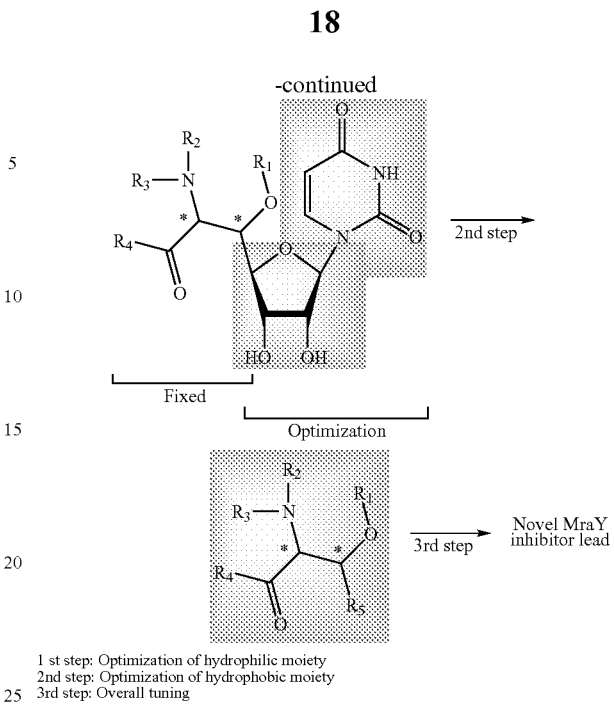

1st step: Optimization of hydrophilic moiety
2nd step: Optimization of hydrophobic moiety
3rd step: Overall tuning A series of uridine-β-hydroxyaminoesters possessing 5'S, 2"S (natural) and 5'S, 2"R (unnatural) stereochemistries can be synthesized from the same intermediate. As illustrated in Scheme B, (5'S, 2"R)-2"-chloro-5'-hydroxy ester 3 can be used to access ia and ib by $S_N2$ type reactions of the 2"-chloro and the epoxy compound. The anti-aldol product 3 was synthesized by diastereoselective anti-aldol reaction between the (−)-N,N-dibenzylnorephedrine derivative 1 and the uridyl aldehyde 2.

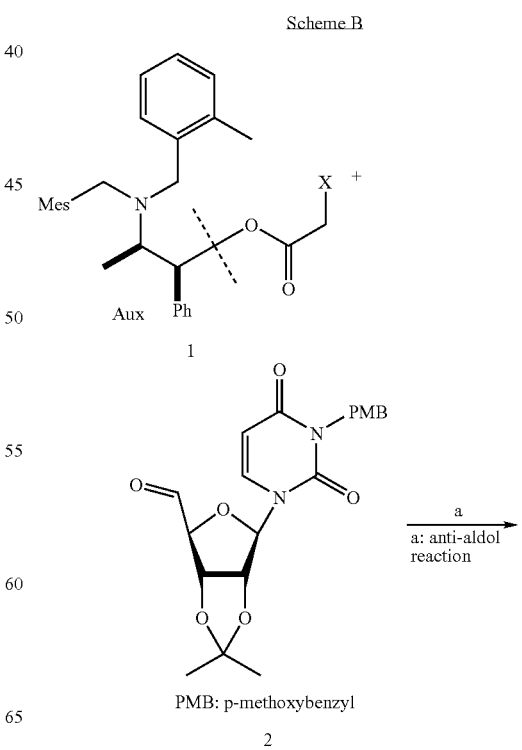

PMB: p-methoxybenzyl

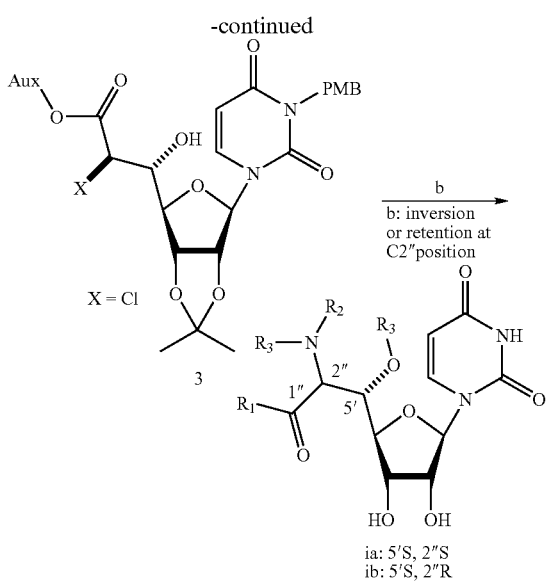

In spite of abundant examples of the utility of syn-2-chloro-3-hydroxy ester units, which is synthesized by the Evans' procedure through the diastereoselective syn-aldol reactions of the chiral oxazolidinones, no efficient diastereoselective or reagent controlled asymmetric anti-aldol reaction to construct anti-2-chloro-3-hydroxycarbonyl units is known. In addition it is desirable to devise hydrolytically stable ester which enables to functionalize at the C2-position with diversity structure of amine derivatives even at elevated temperatures without the formation of undesired by-products such as free carboxylic acid and amides. The present inventors have established highly diastereofacial anti-aldol reactions with 2-(N-2-methylbenzyl-N-2,4,6-trimethylbenzyl)-amino-1-phenylpropanol ester (3, X=alkyl in Scheme B); in these reactions LDA-Cp$_2$ZrCl$_2$ or (c-hexyl)$_2$BOTf/Et$_3$N was utilized to achieve what appears to be exclusive E(O,R)-enolate formations. The anti-2-alkyl-3-hydroxycarboxylic acid esters generated under these conditions were stable in the presence of primary and secondary amines at 90° C. over 12 h. Through NOESY experiments and molecular modeling the origin of the diastereofacial selectivity and hydrolytical stability can be attributed to the following factors. The bulky mesityl group on nitrogen is on the sterically less demanding site. Because of a significant steric interaction between the mesityl group and methyl of o-methylbenzyl group the methyl group of o-methylbenzyl locates toward the ester moiety. Thus re-face is hindered from the approach of electrophiles and nucleophiles. The LDA-Cp$_2$ZrCl$_2$ system forms E(O,R)-zirconium enolate of 3 (X=Me in Scheme B). Similarly, kinetically controlled boron enolate formation of 3 using (c-hexyl)$_2$BOTf/Et$_3$N generates E(O,R)-boron enolate stereoselectively.

Scheme C

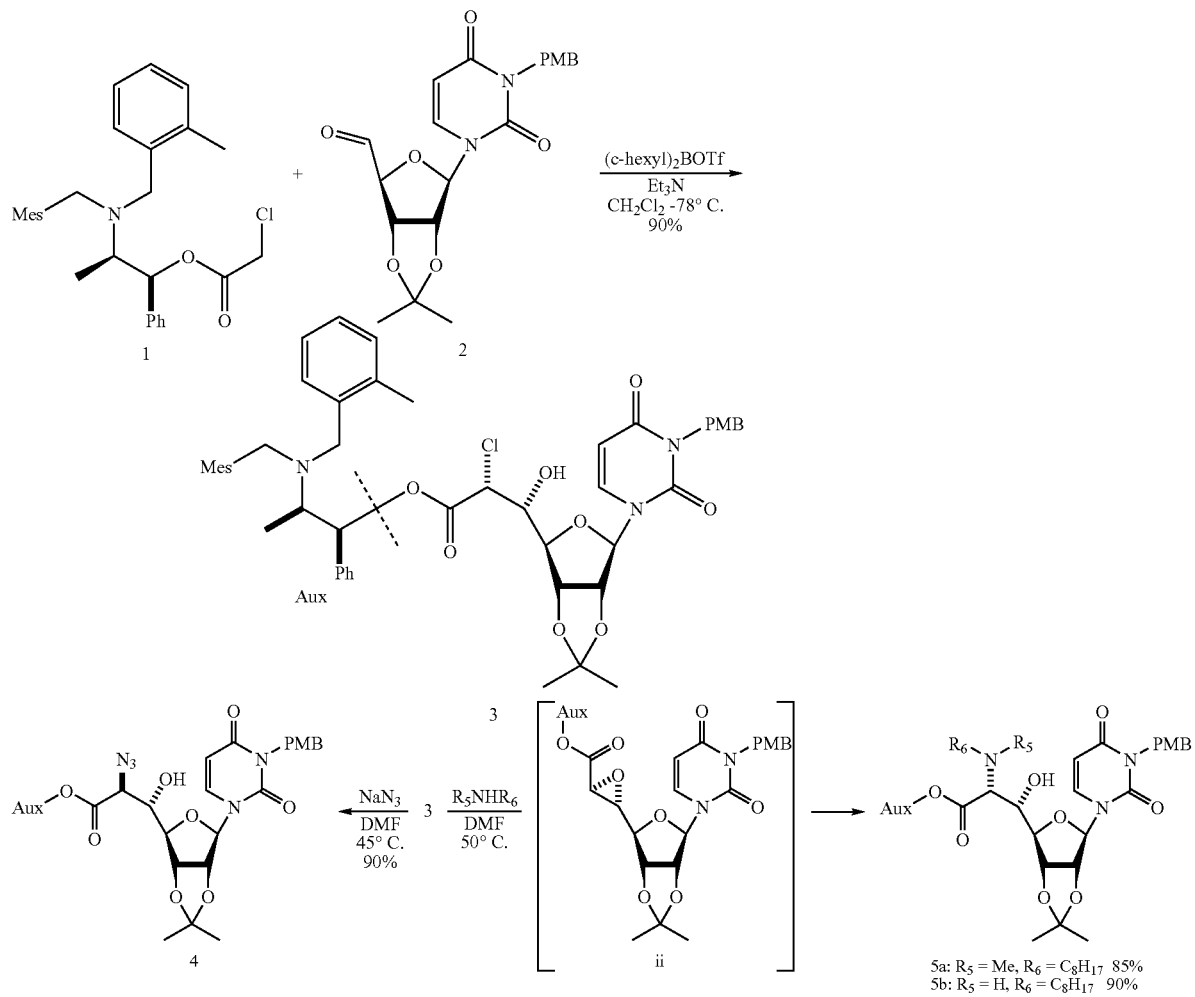

The boron-mediated ((c-hexyl)$_2$BOTf/Et$_3$N) aldol reaction between 1 (X=Cl) and 2 furnished the desired anti-chloro-hydroxy ester 3 (X=Cl) in 90% yield without other detectable diastereomers (Scheme C). Although the epoxide formation of anti-2-halo-3-hydroxycarbonyls is generally entropically favored process, the anti-2-chloro-3-hydroxyester 3 is stable under pH values of 6.0~8.5 for a prolonged time. The nitrogen atom could be introduced to 3 via a S$_N$2 reaction of azide anion at 45° C. to furnish the azido-alcohol 4 without observation of the competitive retro-aldol reaction. The treatment of 3 with primary amines and secondary amines in DMF at 50° C. furnished the epoxide as an intermediate which then underwent the opening of epoxide at α-position to ester carbonyl to yield the amino-alcohol 5. Thus, the uridine-β-hydroxyaminoesters possessing natural and unnatural stereochemistries were prepared from the same intermediate 3.

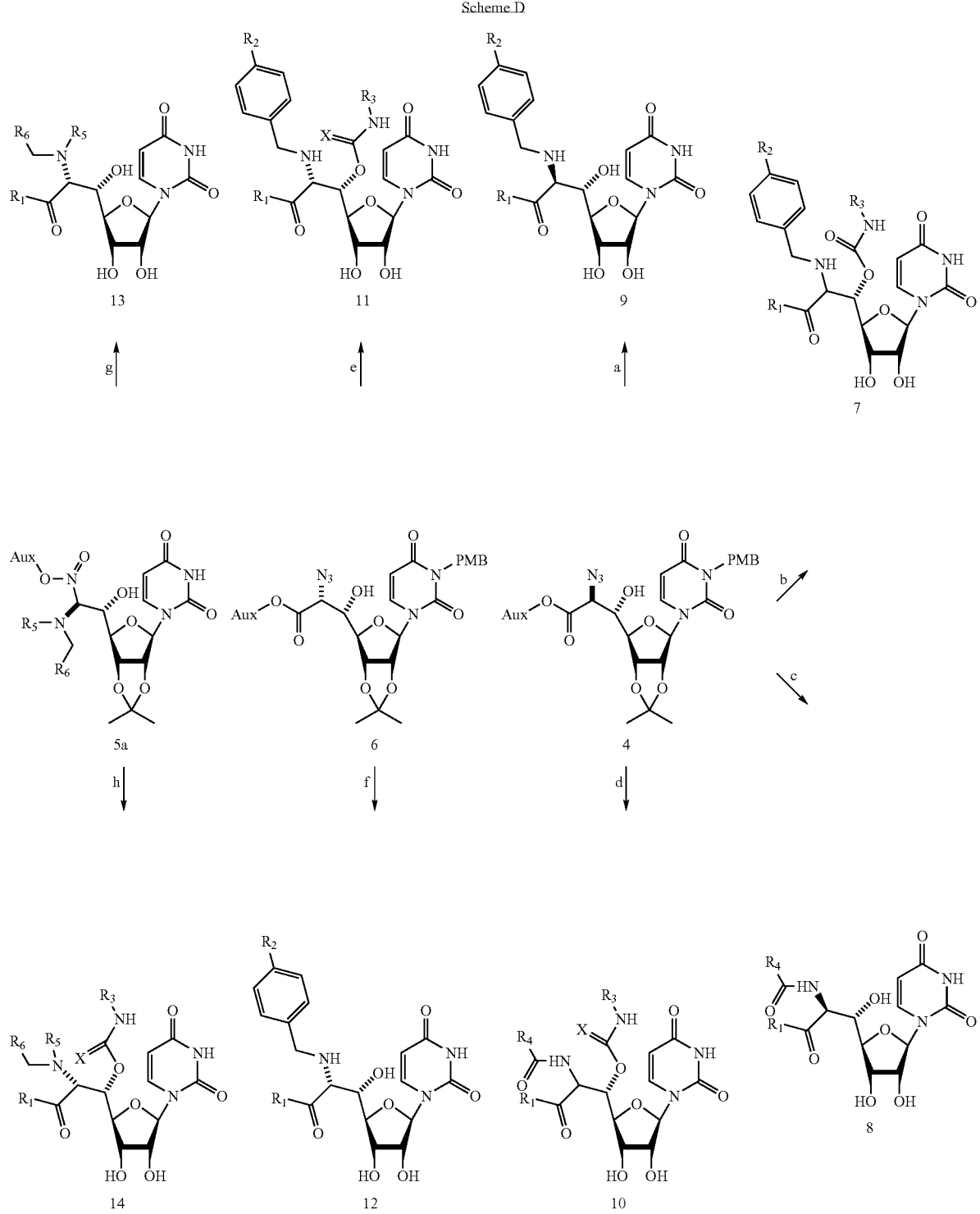

Scheme D

-continued $R_1$ = OH, NH(CH$_2$)$_3$N(Me)Ph, and many others
$R_2$ = I, OMe, and alkyl
$R_3$ = H or Ph
$R_4$ = C$_8$H$_{17}$ or Ph
$R_5$ = H or Me
$R_6$ = C$_7$H$_{15}$ or Ph
X = O or S Deprotection conditions:
a. 1) CAN, CH$_3$CN.; 2) TsOH-H$_2$O, wet acetone., 3) LiOH, THF-water
b.) CAN, CH$_3$CN.; 2) TsOH-H$_2$O, wet acetone., 3) H$_2$, Pd-C, EtOAc
c. 1) CAN, CH$_3$CN.; 2) TsOH-H$_2$O, wet acetone., Reagents and conditions: a. for $R_1$ = OH, $R_2$ = I. 1) PMe$_3$, THF-water, 2) 4-I-benzaldehyde.; Ti(O$^i$Pr)$_4$, NaBH$_4$, THF, 45% for two steps.; 3) deprotection conditions a, 40%.; b $R_1$ = OH, $R_2$ = I, $R_3$ = H, X = O. 1) TMSNCO, THF, 98%.; 2) PMe$_3$, THF-water.; 3) 4-I-benzaldehyde.; Ti(O$^i$Pr)$_4$, NaBH$_4$, THF, 40% for two steps.; 3) deprotection conditions a, 40%.; c for $R_1$ = NH(CH$_2$)$_3$N(Me)Ph, $R_4$ = C$_8$H$_{17}$. 1) PMe$_3$, THF-water.; 2) C$_8$H$_{17}$COOH, PyBOP, HOBt, $^i$Pr$_2$NEt, THF, 94%.; 3) LiOH, THF-water.; 4) $R_1$ = NH(CH$_2$)$_3$N(Me)Ph, PyBOP, HOBt, $^i$Pr$_2$NEt, THF, for 85% for two steps.; 4) deprotection conditions b. 40%; d for $R_1$ = OH, $R_3$ = H, $R_4$ = C$_8$H$_{17}$. 1) TMSNCO, THF, 98%.; 2) PMe$_3$, THF-water.; 3) C$_8$H$_{17}$COOH, PyBOP, HOBt, $^i$PrNEt, THF, 95%.; 4) LiOH, THF-water, 5) $R_1$ = NH(CH$_2$)$_3$N(Me)Ph, PyBOP, HOBt, $^i$Pr$_2$NEt, THF, 93%.; 5) deprotection conditions c, 60%.; e $R_1$ = OH, $R_2$ = H, $R_3$ = H, X = O. 1) TMSNCO, THF, 98%.; 2) PMe$_3$, THF-water.; 3) benzaldehyde.; Ti(O$^i$Pr)$_4$, NaBH$_4$, THF, 40% for two steps.; 3) deprotection conditions a, 40%.; f for $R_1$ = NH(CH$_2$)$_3$N(Me)Ph, $R_2$ = H. 1) PMe$_3$, THF-water.; 2) benzaldehyde.; Ti(O$^i$Pr)$_4$, NaBH$_4$, THF, 43% for two steps.; 3) LiOH, THF-water.; 4) $R_1$ = NH(CH$_2$)$_3$N(Me)Ph, PyBOP, HOBt, $^i$Pr$_2$NEt, THF, for 85% for two steps.; 4) deprotection conditions c. 45%; g for $R_1$ = NH(CH$_2$)$_3$N(Me)Ph, $R_5$ = Me, $R_6$ = C$_7$H$_{15}$. 1) LiOH, THF-water.; 2) $R_1$ = NH(CH$_2$)$_3$N(Me)Ph, PyBOP, HOBt, $^i$Pr$_2$NEt, THF, for 85% for two steps.; 3) deprotection conditions c. 40%; h. for $R_1$ = OH, $R_3$ = Ph, $R_5$ = Me, $R_6$ = C$_7$H$_{15}$, X = S. 1) PhCSO, THF, 98%.; 2) deprotection conditions a, 40%.

The generation of small optimized library was demonstrated by using 4, 6, and 5a. As summarized in Scheme D, the C5' alcohol of 4 was functionalized with isocyanates and thioisocyanates to form the corresponding urethanes and thiourethanes 7 and 10 after deprotection followed by purification. Reduction of the azide group was accomplished by PMe$_3$ in aqueous THF. The generated amine was functionalized by reductive amination and acylations. As expected the carboxylic acid group was utilized for the formation of amide. Similarly, the epimer 6 of 4 at C2" position was converted to the corresponding analogs 11 and 12. N,N-dialkyl amine 5a was functionalize at C5' and C1" positions to furnish 13 and 14 after deprotection.

One of the linkers of the invention, (2-chloro-4-methoxyphenyl)(2,4-dichlorophenyl)methanol 16 was used to immobilize carboxylic acids. The linker was stable under a Boc-deprotection conditions (TsOH.H$_2$O/THF—CH$_2$Cl$_2$). In addition, unlike photolytic (350 nm, 72 h) or Pd-mediated or base-catalyzed cleavage of linkers, the esters of linker 16 was efficiently be cleaved via volatile acids such as 30% TFA/CH$_2$Cl$_2$ or HF.pyridine within 1 h. The progress of each step was conveniently be monitored by LC-MS after the treatment of such Brønsted acids followed by evaporation of volatiles.

Scheme E

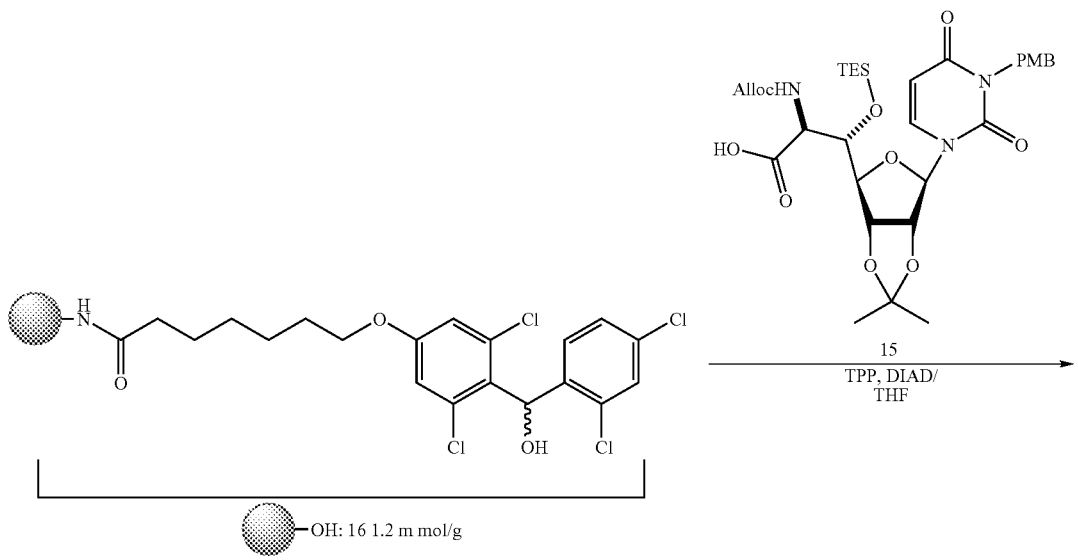

-continued

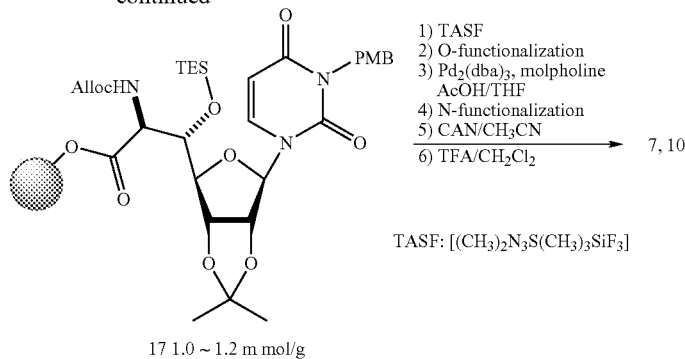

17 1.0 ~ 1.2 m mol/g

In order to facilitate synthesis of a combinatorial library of compounds, the functionalization reaction on the polymer support was used. As illustrated in Scheme E, the carboxylic acid was loaded onto the polymer 16 by using Mitsunobu reaction to furnish 17 whose loading yield was established to be over 83% by the cleavage of the linker followed by $^1$H-NMR analysis of the crude product using an internal standard. The TES group was selectively deprotected with TASF and the generated alcohol was functionalized with TMSNCO in THF in substantially quantitative yield based on $^1$H-NMR analysis. Pd-mediated deprotection of the Alloc group provided the free amine. N-functionalizations on the polymer support were achieved by a reductive amination with benzaldehyde under NaCNBH$_4$ in the presence of HCO$_2$H in THF-MeOH and an amide-formation with nonanoic acid via PyBOP as a coupling reagent. Deprotection of the PMB group with CAN followed by simultaneous deprotections of the acetonide and the linker with TFA provided 7 and 10 in 45% and 40% overall yields, respectively. It should be appreciated a large membered library can be generated using methods disclosed herein by using split-pool synthesis with a large number of building blocks.

General Methods.

Unless indicated or implied otherwise, all glassware was oven dried, assembled hot and cooled under a stream of nitrogen before use. Reactions with air sensitive materials were carried out by standard syringe techniques. Commercially available reagents were used as received without further purification. Thin layer chromatography was performed using 0.25 mm silica gel 60 (F254, Merck) plates visualizing at 254 nm, or developed with potassium permanganate solutions by heating with a hot-air gun. Specified products were purified by flash column chromatography using silica gel 60 (230-400 mesh, Merck). IR absorptions on NaCl plates were run on a Perkin Elmer FT-IR 1600. $^1$H NMR spectral data were obtained using Varian 300, 400 or 500 MHz instruments. The residual solvent signal was utilized as an internal reference. $^{13}$C NMR spectral data were obtained using a Varian 75 or 100 or 125 MHz spectrometer. Chemical shifts were reported in parts per million (ppm) downfield from TMS, using the middle resonance of CDCl$_3$ (77.0 ppm) as an internal standard. For all NMR spectra, δ values are given in ppm and J values in Hz. Optical rotations were taken using Rudolph research—Autopol III, automatic polarimeter.

Synthesis of (1S,2R)-2-((2-methylbenzyl)(2,4,6-trimethylbenzyl)amino)-1-phenylpropyl-2-chloroacetate (1)

2-(N-2-methylbenzyl-N-2,4,6-trimethylbenzyl)-amino-1-phenylpropanol was synthesized from (1R, 2S)-(−)-norephedrine according to the procedure described by Abiko et al., in J. Am. Chem. Soc., 1997, 119, 2586. To a stirred solution of 2-(N-2-methylbenzyl-N-2,4,6-trimethylbenzyl)-amino-1-phenylpropanol (5 g, 12.9 mmol) in CH$_2$Cl$_2$ (30 mL) at 0° C. was added DMAP (3.15 g, 25.8 mmol) and 2-chloroacetyl chloride (2.17 g, 19.4 mmol). The reaction mixture was stirred for 1 h and quenched with aq. NaHCO$_3$, and extracted with EtOAc. The combined extracts were washed with brine, dried over Na$_2$SO$_4$, and concentrated in vaccuo. The residue was purified by silica gel chromatography (2:1, hexanes: EtOAc) to afford 1 (5.67 g, 12.2 mmol, 95%). $^1$H-NMR (CDCl$_3$, 400 MHz) δ 1.30 (d, J=7.2 Hz, 3H), 2.09 (s, 9H), 2.26 (s, 3H), 3.28 (m, 1H), 3.56 (m, 2H), 3.71 (m, 2H), 4.02 (m, 2H), 6.05 (d, J=7.2 Hz, 1H), 6.82 (s, 2H), 6.91 (m, 2H), 7.18 (m, 7H). $^{13}$C-NMR (CDCl$_3$, 100 MHz) 9.2, 19.2, 20.1, 20.9, 41.1, 47.6, 51.2, 56.2, 79.1, 129.4, 127.0, 127.3, 127.8, 128.1, 129.0, 130.2, 130.8, 131.4, 136.4, 136.8, 137.4, 138.5, 166.4. LR-MS (ESI): C$_{29}$H$_{34}$ClNO$_2$ (M+H$^+$) found 264.2. [α]$_D$=−15.1° (c 0.8, CHCl$_3$, 25° C.).

Synthesis of the Anti-chlorohydroxy Ester 3

To a stirred solution of 1 (2.43 g, 5.25 mmol) was dissolved in CH$_2$Cl$_2$ (50 mL) and cooled to −78° C. Into the reaction mixture Et$_3$N (1.8 mL, 13.0 mmol) followed by (c-hexyl)$_2$BOTf (9.15 mL, 1.21 M solution in dichloroethane) were added. After being stirred for 2 h at −78° C., the uridine-aldehyde 2 (750 mg, 1.85 mmol) was added. The reaction mixture was stirred for 1 h at the same temperature and quenched with pH 7.3 phosphate buffer. The water phase was extracted with CH$_2$Cl$_2$. The combined extracts were washed with brine, dried over Na$_2$SO$_4$, and concentrated in vaccuo. The residue was purified by silica gel chromatography (2:1, hexanes:EtOAc) to afford 3 (1.44 g, 1.67 mmol, 90%). $^1$H-NMR (CDCl$_3$, 300 MHz) δ 1.35 (m,3H), 1.53 (s, 3H), 1.59 (s, 3H), 2.10 (s, 9H), 2.25 (s, 3H), 3.58 (m, 3H), 3.70 (m, 1H), 3.78 (s, 3H), 3.98 (d, J=7.2 Hz, 1H), 4.24 (m, 3H), 5.01 (m, 4H), 5.45 (d, J=2.1 Hz, 1H), 5.76 (d, J=7.8 Hz, 1H), 6.09 (d, J=6.6 Hz, 1H), 6.75 (s, 2H), 6.82 (d, J=10 Hz, 2H ), 6.93 (m, 2H), 7.17 (m, 8H), 7.42 (d, J=10.0 Hz, 2H). $^{13}$C-NMR (CDCl$_3$, 75 MHz) 9.3, 14.1, 19.2, 20.1, 20.8, 25.3, 27.2, 43.5, 47.3, 51.1, 54.9, 55.1, 56.6, 60.3, 72.5, 78.9, 79.1, 83.9, 86.1, 96.4, 102.4, 113.7, 114.6, 125.3, 126.9, 127.6, 128.0, 128.5, 129.0, 130.1, 130.6, 130.9, 131.0, 131.5, 136.3, 136.8, 137.4, 138.3, 138.4, 138.7, 140.4, 150.9, 159.1, 162.2, 167.3. LRMS (ESI) $C_{49}H_{56}O_9N_3Cl$ found 866.2. $[\alpha]_D = +8.0$ (c 0.05, $CHCl_3$, 25° C.).

Synthesis of the Azide-alcohol 4

To a stirred solution of 3 (135 mg, 0.16 mmol) in DMF (10 mL) was added $NaN_3$ (52.0 mg, 0.80 mmol). The reaction mixture was stirred at 45° C. for 45 min and quenched with water. The water phase was extracted with EtOAc. The combined extracts were washes with brine, dried over $Na_2SO_4$, and concentrated in vaccuo. The residue was purified by silica gel chromatography (3:1, hexanes:EtOAc) to afford 4 (126 mg, 0.14 mmol, 90%). $^1$H-NMR ($CDCl_3$, 300 MHz) δ 1.35 (m, 3H), 1.54 (s, 3H), 1.56 (s, 3H), 2.10 (s, 9H), 2.23 (s, 3H), 3.08 (d, J=6.6 Hz, 1H ), 3.59 (m, 3H), 3.76 (m, 1H), 3.79 (s, 3H), 3.96 (m, 1H), 4.45 (m, 1H), 4.51 (d, J=2.7 Hz, 1H), 5.01 (m, 4H), 5.41 (d, J=2.1 Hz, 1H), 5.76 (d, J=7.8 Hz, 1H), 6.13 (d, J=6.6 Hz, 1H), 6.74 (s, 2H), 6.84 (m, 2H), 6.93 (m, 2H), 7.17 (m, 8H), 7.42 (m, 2H). $^{13}$C-NMR ($CDCl_3$, 75 MHz) 14.2, 19.2, 20.1, 20.8, 25.1, 27.0, 31.6, 43.5, 47.5, 51.2, 55.2, 60.4, 63.2, 71.4, 72.0, 79.4, 81.2, 83.9, 87.7, 97.9, 102.5, 113.7, 114.4, 125.4, 127.0, 127.2, 127.9, 128.1, 128.5, 129.0, 130.2, 130.6, 130.9, 131.4, 136.3, 136.8, 137.3, 138.3, 141.1, 150.6, 159.1, 162.2, 167.1, 168.1, 171.2.

LRMS (ESI) $C_{49}H_{56}O_9N_6$ found 873.4 $[\alpha]_D = +19.0°$ (c 2.0, $CHCl_3$, 25° C.)

Synthesis of 5a

To a stirred solution of 3 (30 mg, 0.036 mmol) in DMF (2 mL) was added N-methyl butylamine (15.7 mg, 0.18 mmol). The reaction mixture was stirred at 50° C. for 12 h. All volatiles were evaporated in vaccuo. The residue was purified by silica gel chromatography (3:1, hexanes:EtOAc) to afford 5a (29.8 mg, 0.032 mmol, 90%). $^1$H-NMR ($CDCl_3$, 300 MHz) δ 0.97 (t, J=7.2 Hz, 3H), 1.33 (m, 7H), 1.54 (s, 3H), 1.59 (m, 3H), 2.01 (s, 9H), 2.14 (s, 3H), 2.25 (s, 3H), 2.69 (m, 2H), 3.58 (m, 3H), 3.70 (m, 1H), 3.78 (s, 3H), 4.26 (m, 3H), 4.40 (m, 1H), 5.00 (m, 4H), 5.49 (d, J=2.4 Hz, 1H), 5.76 (d, J=8.1 Hz, 1H), 6.04 (d, J=8.4 Hz, 1H), 6.73 (m, 2H), 6.82 (m, 2H), 6.93 (m, 2H), 7.11 (m, 8H), 7.40 (m, 2H). LRMS (ESI) $C_{54}H_{68}O_9N_4$ found=917.5. $[\alpha]_D = +12°$ (c 0.1, $CHCl_3$, 25° C.).

Synthesis of the Azide-alcohol 6

To a stirred solution of 3 (30.0 mg, 0.035 mmol) in benzene (1.0 mL) was added DBU (10.7 mg, 0.070 mmol). After 15 min the reaction mixture was in vaccuo to furnish the crude epoxide. This was dissolved in DMF (1.0 mL) and added $NaN_3$ (11.7 mg, 0.18 mmol) and $NH_4Cl$ (19.0 mg, 0.35 mmol). The reaction mixture was stirred at 90° C. for 1 h and quenched with water. The water phase was extracted with EtOAc. The combined extracts were washed with brine, dried over $Na_2SO_4$, and concentrated in vaccuo. The residue was purified by silica gel chromatography (3:1, hexanes:EtOAc) to afford 6 (26.0 g, 0.029 mmol, 85%). $^1$H-NMR ($CDCl_3$, 300 MHz) δ 1.35 (m, 3H), 1.54 (s, 3H), 1.56 (s, 3H), 2.10 (s, 9H), 2.23 (s, 3H), 3.08 (d, J=6.6 Hz, 1H), 3.59 (m, 3H), 3.76 (m, 1H), 3.79 (s, 3H), 3.96 (m, 1H), 4.45 (m, 1H), 4.51 (d, J=2.7 Hz, 1H), 5.01 (m, 4H), 5.41 (d, J=2.1 Hz, 1H), 5.76 (d, J=7.8 Hz, 1H), 6.13 (d, J=6.6 Hz, 1H), 6.74 (s, 2H), 6.84 (m, 2H), 6.93 (m, 2H), 7.17 (m, 8H), 7.42 (m, 2H). $^{13}$C-NMR ($CDCl_3$, 75 MHz) 14.2, 19.2, 20.1, 20.8, 25.1, 27.0, 31.6, 43.5, 47.5, 51.2, 55.2, 60.4, 63.2, 71.4, 72.0, 79.4, 81.2, 83.9, 87.7, 97.9, 102.5, 113.7, 114.4, 125.4, 127.0, 127.2, 127.9, 128.1, 128.5, 129.0, 130.2, 130.6, 130.9, 131.4, 136.3, 136.8, 137.3, 138.3, 141.1, 150.6, 159.1, 162.2, 167.1, 168.1, 171.2.

LRMS (ESI) $C_{49}H_{56}O_9N_6$ found 873.4 $[\alpha]_D = +5.0°$ (c 1.0, $CHCl_3$, 25° C.).

Example 2

Acid- and Base-Stable Esters: Protecting Group for Carboxylic Acids

As summarized in Scheme 2-1, (4-methoxyphenyl) (chlorophenyl)methanols 4a-d were conveniently synthesized by Friedel-Crafts reactions followed by $NaBH_4$ reductions, could be efficiently esterified by using EDCI, DCC, IDC or acid chloride methods. The tetrachloro-substituted 4-methoxydiphenylmethyl esters 4d showed a surprising and unexpected acid stability. For example, no regeneration of the acids from the esters 4d was observed under 20% TsOH for over 36 h.

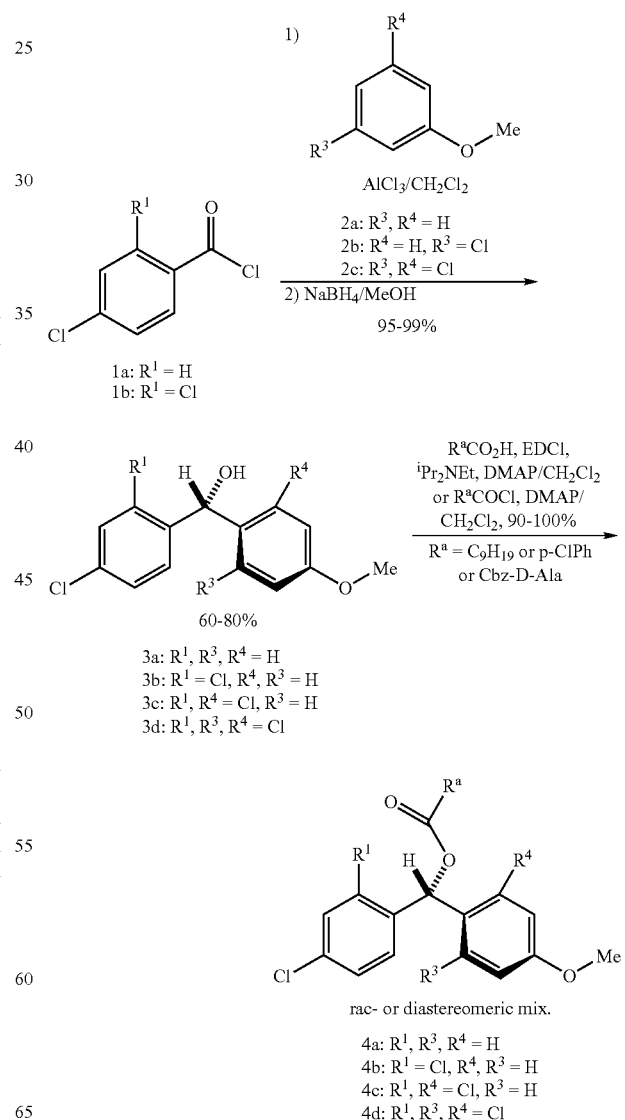

Scheme 2-1

As summarized in Table 2-1, the esters 4d ($R_4$=$CH_3$ or $C_8H_{17}$) also exhibited excellent stability to a variety of Brønsted and Lewis acids such as 15% TFA, 30% HF, 2N HCl, HBr/AcOH, $TiCl_4$, $ZnCl_2$, $AlCl_3$, $B(C_6F_5)_3$, $BCl_3$, $BBr_3$, $BF_3$·$OEt_2$, TMSOTf, and $La(OTf)_3$ at rt. Moreover, the esters 4d showed stability under basic conditions, e.g., no saponifications were observed under $NH_4OH$ (40% in aq THF), LiOH (10% in aq THF-MeOH), NaOH (6N in aq MeOH), TlOEt (in aq THF), and DBU (10% in aq THF) at rt for over 24 h. The esters 4d also showed excellent stability to nucleophiles, e.g., no significant nucleophilic attack was observed on the esters 4d by primary and secondary amines [in aq THF at 80° C.), $NH_2NH_2$ (in aq THF at rt), alkylthiols (in THF at 80° C.), $NaN_3$ (90° C. in DMF), $H_2O_2$/NaOH (aq THF at rt), and MeMgBr (0° C. to rt), 3]; and no significant enolate formation was observed with LDA, NaHMDS, KHMDS, and "$Bu_2$BOTf/$^i$$Pr_2$NEt at −78° C. to rt. In addition, the esters 4d were stable under a variety of reducing conditions such as Zn/HCl, Ag(Hg), $B_2H_6$, $NaBH_4$ (60° C. in MeOH), Li(O$^t$Bu)$_3$AlH, Raney Ni, $H_2$/RhCl(TPP)$_3$, and $H_2$/Pd—C (in EtOAc or 1,4-dioxane). The esters 4d remained intact under Pd-mediated coupling reactions (Suzuki-Miyaura and Heck reactions). The esters 4d did not show any significant reaction with $I_2$ and NBS. The esters 4d were photolytically stable, e.g., no change was observed when irradiated with wavelength of 200~350 nm (in dioxane for 72 h).

TABLE 2-1

Reactivities of the ester 4d ($R_4$ = $CH_3$ or $C_8H_{17}$) against a variety of reagents[q]

| 20% TsOH[a] | 2N HCl[b] | 30% HF[b] | 15% TFA[c] | HBr/AcOH | BCl$_3$[c] | BBr$_3$[c] | TMSOTf[c] | AlCl$_3$[c] | B(C$_6$F$_6$)$_3$[c] | La(OTf)$_3$[c] |
|---|---|---|---|---|---|---|---|---|---|---|
| L | L | L | L | L | L | L | L | L | L | L |

| TiCl$_4$[c] | ZnCl$_2$[c] | 10% BF$_3$·OEt$_2$[c] | LiOH/THF[d] | 6N aq NaOH[e] | 1N aq NaOH, 50° C. | TlOEt[g] | NH$_4$OH[h] | N$_2$H$_4$[g] | DBU[g] |
|---|---|---|---|---|---|---|---|---|---|
| L | L | L | L | L | M[f] | L | L | L | L |

| H$_2$O$_2$/NaOH[g] | "Bu$_2$NH[i] | "BuNH$_2$[i] | "BuSH[i] | NaN$_3$[j] | MeMgBr[k] | "BuLi[l] | NaHMDS[m] | KHMDS[m] | "Bu$_2$BOTf[n] | Zn/HCl[o] |
|---|---|---|---|---|---|---|---|---|---|---|
| L | L | L | L | L | L | M | L | L | L | L |

| Al(Hg)[o] | B$_2$H$_6$[k] | NaBH$_4$[p] | $^i$Pr$_2$AlH[c] | LiAlH$_4$[k] | Li(O$^t$Bu)$_3$AlH[k] | H$_2$/Pd—C/EtOAc | H$_2$/Pd—C/1,4-dioxane | H$_2$/RhCl(TPP)$_3$ |
|---|---|---|---|---|---|---|---|---|
| L | L | L | H | H | L | L | L | L |

| Raney Ni[o] | PhB(OH)$_2$/Pd(TPP)$_4$/TlOEt[g] | PhCH=CH$_2$/Pd$_2$(dba)$_3$/$^n$Bu$_3$P•HBF$_4$/$^i$Pr$_2$NEt[k] | I$_2$[h] | NBS[k] | hv (200~350 nm)[o] |
|---|---|---|---|---|---|
| L | L | L | L | L | L |

[a] in CH$_2$Cl$_2$-THF (1:1).;

[b] in CH$_3$CN.;

[c] in CH$_2$Cl$_2$.;

[d] at 50° C. for over 1 h.;

[e] at rt for over 36 h.;

[f] 50% of regeneration of 3d (Scheme 1).;

[g] in aq THF.;

[h] in aq THF-MeOH (1:1).;

[i] in THF at 80° C.;

[j] in DMF at 90° C.;

[k] in THF at rt for over 1 h.;

[l] ~70% of 4d was recovered after 1 h at −78° C.;

[m] in THF at −78° C. to 0° C. for over 1 h.;

[n] in CH$_2$Cl$_2$ in the presence of $^i$Pr$_2$NEt.; [o] in 1,4-dioxane.;

[p] in MeOH at 60° C.

[q] H indicates the protecting group is readily cleaved.; M indicates that the protecting group was cleaved very slowly.; L indicates that the protecting group was stable.

Scheme 2-A

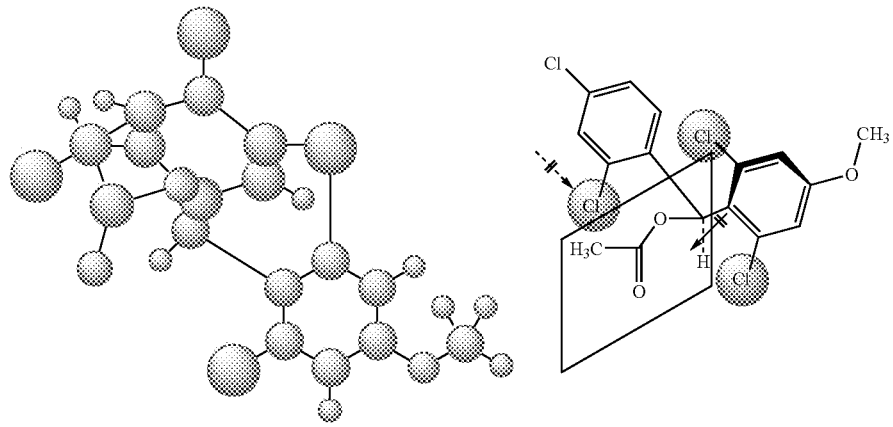

Chem3D representation of the
X-ray crystal structure of 4d (R$_4$ = CH$_3$)

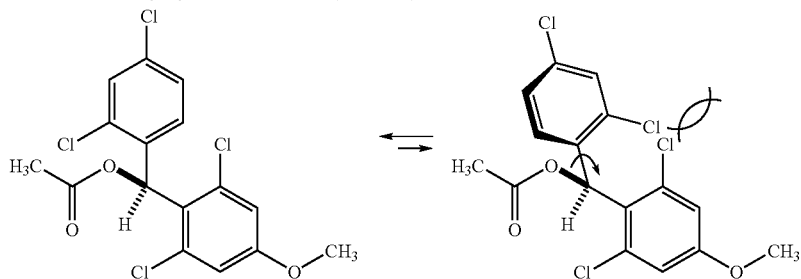

A lowest energy conformer of 4d (R$_4$=CH$_3$) was analyzed by single crystal X-ray analysis. The X-ray showed that the dihedral angles formed by two planar chlorosubstituted-benzenes and by —CO—O— linkage and the ether methine proton are 83.5° and 159.8°, respectively. Without being bound by any theory, it is believed that there is a significant electronic repulsion between the o-chloro atoms in two benzene rings. The o-chloro atom in dichlorobenzene is located towards the carbonyl ester plane. See Scheme 2-A. Thus, it is believed that the chloro atoms at o-positions in two benzenes hinder nucleophilic attacks at the ester carbonyl from both re- and si-faces. In addition, it is believed that the 3,5-dichloro atoms in the anisole moiety attenuate an electron donating character of the methoxy group. One or more of these factors are believed to be responsible for the stability of the esters 4d against bases, nucleophiles, and acids.

The esters 4d was removed (e.g., cleaved) by using 20% TFA in CH$_2$Cl$_2$ to afford the corresponding acids (R$_4$CO$_2$H) and the trifluoroacetate 5a in substantially quantitative yields. The trifluoroacetate 5a was also stable under most acidic conditions tested in Table 1 and SiO$_2$, but could easily be cleaved by aq NH$_3$ in THF-MeOH within 3 h to regenerate 3d in quantitative yield (Scheme 2-2). Alternatively, the esters 4d were cleaved by a hydrogenation reaction with H$_2$/Pd—C (in MeOH) to regenerate the carboxylic acids, and reduced by LiAH$_4$ or DIBAL-H to afford the corresponding alcohols (R$_4$=C$_9$H$_{19}$ and p-ClPh) in high yields (Table 2-1).

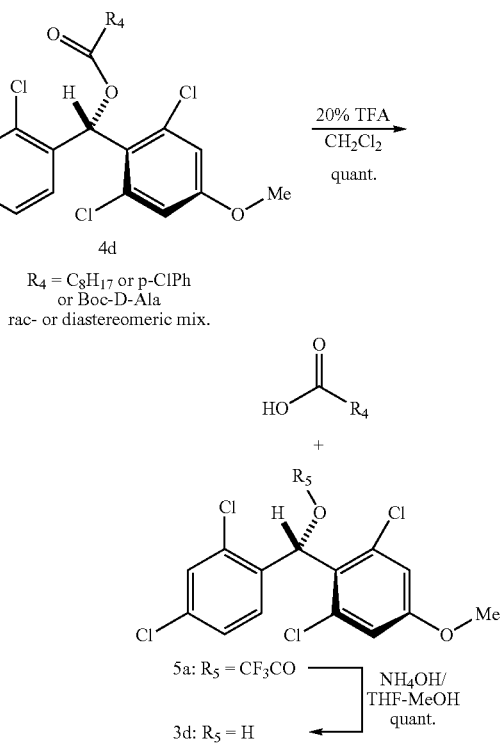

Scheme 2-2

General Methods

Unless indicated or implied otherwise, IR absorptions on NaCl plates were run on a Perkin Elmer FT-IR 1600. $^1$H NMR spectral data were obtained using Varian 300, 400 MHz instruments. The residual solvent signal was utilized as an internal reference. $^{13}$C NMR spectral data were obtained using a Varian 100 MHz spectrometer. Chemical shifts were reported in parts per million (ppm) downfield from TMS, using the middle resonance of CDCl$_3$ (77.0 ppm) as an internal standard. For all NMR spectra, δ values are given in ppm and J values in Hz. Reagents and solvents are commercial grade and were used as supplied. Reaction vessels were flame-dried or oven-dried and cooled under an inert atmosphere when necessary.

(2,6-dichloro-4-methoxyphenyl)(2,4-dichlorophenyl) methanol (3d)

Anhydrous AlCl$_3$ (4.5 g, 33.9 mmol) was placed in a round bottom flask and PhNO$_2$ (150 mL) was added. At −78° C. 2,4-dichlorobenzoyl chloride (4.7 mL, 33.9 mmol) and 3,5-dichloro anisole (5.0 g, 28.2 mmol) were added. The reaction mixture was kept at the same temperature for 1 h and warmed to rt over 24 h. The reaction mixture was diluted with Et$_2$O (50 mL) at 0° C. and quenched with 1N NaOH (~30 mL). The reaction mixture was stirred vigorously until a white precipitate had been formed. The precipitates were filtered and washed with CH$_2$Cl$_2$ (50, 30, and 20 mL). The combined organic solvents were dried (Na$_2$SO$_4$), filtered, and concentrated under vacuum at ~10 mmHg. Purification by silica gel chromatography (4:1, hexanes:CHCl$_3$) to provide (2,6-dichloro-4-methoxyphenyl)(2,4-dichlorophenyl)methanone (8.3 g, 85%) as a white powder. $^1$H NMR (300 MHz, CDCl$_3$): δ 7.68 (d, J=8.2 Hz, 1H), 7.54 (d, J=2.1 Hz, 1H), 7.37 (dd, J=8.1, 2.1 Hz, 1H), 6.95 (s, 2H), 3.87 (s, 3H); $^{13}$C NMR (75 MHz, CDCl$_3$): δ 197.6, 163.8, 142.0, 138.3, 137.7, 136.4, 130.3, 129.9, 127.8, 122.9, 118.4, 117.9, 114.6, 56.1; IR (film): 1619 cm$^{-1}$, 1584, 1553, 1400, 1309; HRMS (FAB): C$_{14}$H$_8$Cl$_4$O$_2$ (M+Na$^1$) calcd. 370.91761, found 370.91765.

(2,6-Dichloro-4-methoxyphenyl)(2,4-dichlorophenyl) methanone (1.0 g, 2.8 mmol) was dissolved in MeOH (15 mL) and cooled to 0° C. NaBH$_4$ (318 mg, 8.4 mmol) was added. The reaction mixture was quenched by aq. NH$_4$Cl (15 mL) and extracted with EtOAc (100, 30, and 20 mL). The combined extracts were washed with brine (15 mL), dried (Na$_2$SO$_4$), and concentrated in vacuo. Purification by silica gel chromatography (5:1, hexanes:EtOAc) to provide 3d (980 mg, 97%) as a white powder. $^1$H NMR (300 MHz, CDCl$_3$): δ 7.69 (d, J=8.4 Hz, 1H), 7.38 (d, J=3.0 Hz, 1H), 7.31 (dd, J=8.2, 3.0 Hz, 1H), 6.91 (s, 2H), 6.61 (d, J=2.1 Hz, 1H), 3.85 (s, 3H); $^{13}$C NMR (75 MHz, CDCl$_3$): δ 159.6, 137.8, 136.3, 133.9, 133.0, 130.5, 129.6, 129.6, 128.0, 126.6, 115.4, 115.4, 70.2, 55.9; IR (film): 3482 cm$^{-1}$, 1438, 1410, 1325; HRMS (FAB): C$_{14}$H$_{10}$Cl$_4$O$_2$ (M+Na$^+$) calcd. 372.93326, found 372.93327.

(2,6-dichloro-4-methoxyphenyl)(2,4-dichlorophenyl) methyl nonanoate; Typical Procedure for Esterification of 3d To a stirred solution of 3d (148 mg, 0.42 mmol) in CH$_2$Cl$_2$ (3.0 mL) was added n-nonanoic acid (84 mg, 0.53 mmol), DIC (98 μL, 0.60 mmol), and DMAP (146 mg, 1.2 mmol). After 3 h at rt, the reaction mixture was quenched by 0.5N HCl (3 mL) and extracted with EtOAc (30 mL). The combined extracts were washed with aq. NaHCO$_3$ (15 mL), brine, dried over Na$_2$SO$_4$, and concentrated in vacuo. Purification by silica gel chromatography (20:1 to 10:1, hexanes:EtOAc) to provide the title nonanoate as a oil (194 mg, 0.39 mmol, 94%). $^1$H-NMR (CDCl$_3$, 300 MHz): δ 7.49 (s,1H), 7.36 (m, 2H), 7.21 (m. 1H), 7.06 (d, J=1.8 Hz, 1H), 6.80 (d, J=2.1 Hz, 1H), 3.72 (s, 3H), 2.42 (t, J=1.8 Hz, 2H), 1.28 (m, 12H), 0.89 (t, J=6.7 Hz, 3H); $^{13}$C-NMR (CDCl$_3$, 75 MHz): δ 172.3, 159.4, 136.2, 135.6, 134.6, 134.0, 133.5, 130.1, 129.4, 126.2, 122.5, 122.3, 111.1, 68.5, 56.2, 34.1, 31.7, 29.2, 29.1, 29.0, 24.8, 22.6, 14.1; IR (film): 1615 cm$^{-1}$, 1428, 1315; HRMS (FAB): C$_{23}$H$_{26}$Cl$_4$O$_3$ (M+Na$^+$) calcd.513.05338, found 513.05340.

(2,6-dichloro-4-methoxyphenyl)(2,4-dichlorophenyl) methyl (2R)-2-(tert-butoxycarbonylamino)propanoate To a stirred solution of 3d (25 mg, 0.071 mmol) in CH$_2$Cl$_2$ (1.0 mL) was added Boc-D-Ala-OH (20 mg, 0.11 mmol), DIC (26 μL, 0.17 mmol), and DMAP (27 mg, 0.22 mmol). After 3 h at rt, the reaction mixture was quenched by 0.5 N HCl (1 mL) and extracted with EtOAc (15 mL). The combined extracts were washed with aq. NaHCO$_3$ (10 mL), brine (10 mL), dried (Na$_2$SO$_4$), and concentrated in vacuo. Purification by PTLC (5:1, hexanes:EtOAc) to provide a diastereomixture of the title (2R)-propanoate (34 mg, 0.065 mmol, 92%) as a solid.

$^1$H-NMR (CDCl$_3$, 400 MHz): δ 7.45 (m, 2H), 7.36 (m, 2H), 7.23 (m. 4H), 7.06 (m, 2H), 6.81 (m, 2H), 5.03 (m, 1H), 4.44 (m, 1H), 3.73 (s, 3H), 3.70 (s, 3H), 1.43 (s, 18H), 1.37 (d, J=7.2 Hz, 3H), 1.15 (d, J=6.4 Hz, 3H); $^{13}$C-NMR (CDCl$_3$, 100 MHz): 170.9, 159.4, 136.4, 136.2, 135.9, 134.4, 134.1, 134.0, 133.9, 133.6, 130.3, 129.5, 129.4, 126.3, 122.6, 122.5, 121.7, 111.1, 79.9, 69.8, 56.2, 56.1, 49.2, 28.3, 18.9, 18.5; IR (film): 1615 cm$^{-1}$, 1610; HRMS (FAB): C$_{22}$H$_{23}$Cl$_4$O$_5$N (M+Na$^+$) calcd. 544.02280, found 544.02282.

Typical Procedure for the Deprotection

The ester of 3d was dissolved in 20% TFA in CH$_2$Cl$_2$ (0.3 M) and kept for 1 h at rt. Volatiles were evaporated in vaccuo to provide the carboxylic acid and 5a. The carboxylic acid was separated from 5d by a silica gel plug (10:1, hexanes: EtOAc to 5:1, CHCl$_3$:MeOH) or a back-extraction procedure [solvent system: EtOAc-water (for the extraction of 5d under a basic condition (NaHCO$_3$), CHCl$_3$-water (for the extraction of the carboxylic acid under an acidic condition (dil. HCl)].

Example 3

High-throughput Synthesis of Substituted Hydrazine Derivatives

MenA (1,4-dihydroxy-2-naphthoate prenyltransferase), the sixth enzyme in menaquinone biosynthesis, is a novel target for the development of new drug leads for MDR Gram-positive pathogens. In the discovery of MenA inhibitors, a library of molecules based on the 4-alkoxydiphenylmethanones were synthesized. This library of compounds contained tertiary, secondary amines and hydrazines and were evaluated in an enzymatic assay in vitro ($IC_{50}$) against MenA, and bacterial growth assays (MIC). From these synthesis-assay processes it was found that the structure of hydrazine significantly influences MenA and bacterial growth inhibitory activities. Thus, in an attempt to deliver target-specific library for the development of MenA inhibitors, it is desirable to diversify the library structure with a variety of hydrazine building blocks. However, generation of such a library has been limited by the lack of availability of diverse structures of hydrazine molecules[4] from commercial sources. To date, no high-throughput synthesis of substituted hydrazine derivatives have been reported.

Compounds of the invention, such as the (2,6-dichloro-4-methoxyphenyl)(2,4-dichlorophenyl)methyl hydrazinecarboxylate derivative 5b (Scheme 3-1), which were conveniently synthesized by Friedel-Crafts reactions followed by $NaBH_4$ reduction, and CDI-mediated urethane formation reactions, are stable to various acidic conditions such as 10~15% TFA, 30% HF, 2N HCl, HBr/AcOH, $TiCl_4$, $ZnCl_2$, $AlCl_3$, $B(C_6F_5)_3$, $BCl_3$, $BBr_3$, TMSOTf, and $La(OTf)_3$ at rt. These compounds are also stable to bases such as 40% $NH_4OH$, 10% LiOH, 6N NaOH, TlOEt, and DBU at rt. Moreover they are stable against and nucleophiles such as primary and secondary amines at 80° C., and $NH_2NH_2$ at rt. However, The urethane 5b could conveniently be deprotected by using 20% TFA in $CH_2Cl_2$ to afford hydrazine.TFA salt and (2,6-dichloro-4-methoxyphenyl)(2,4-dichlorophenyl)methyl 2,2,2-trifluoroacetate in quantitative yields.

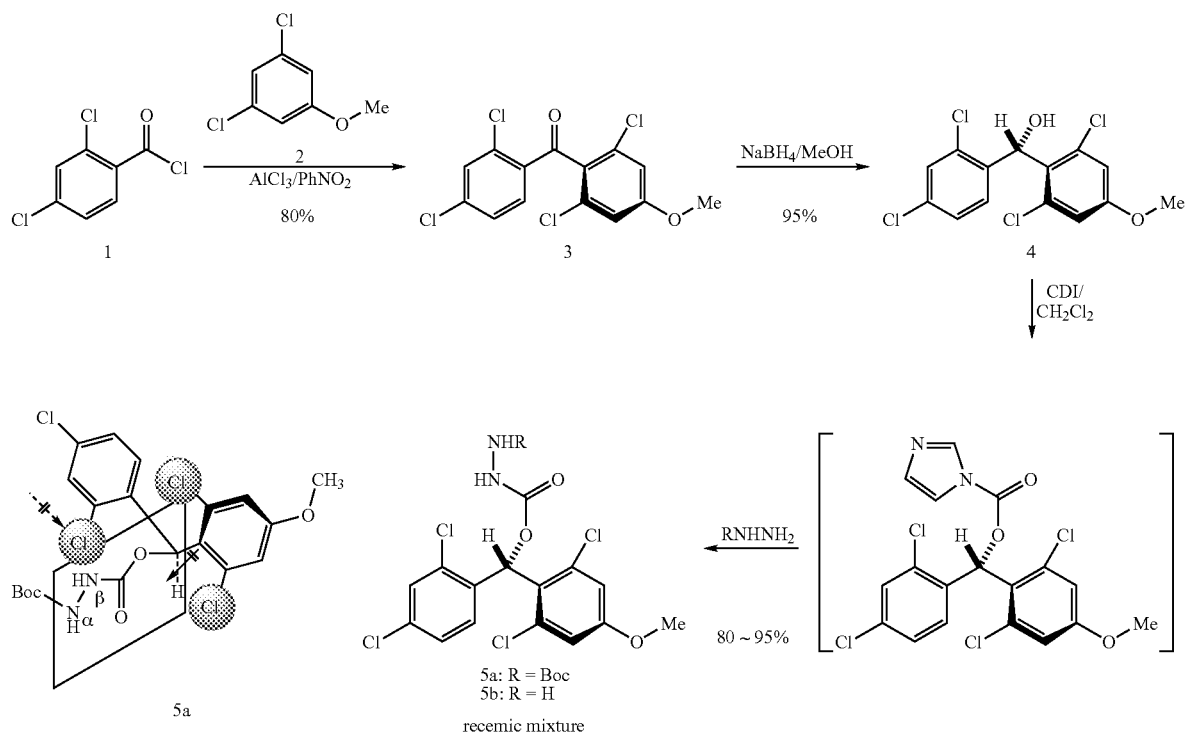

Scheme 3-1

For selective alkylation of functionalized hydrazines on polymer-support (or in solution phase), it is desirable to have a protecting group for hydrazine nitrogen that can be cleaved by a volatile and mild acid (such as TFA) and yet is stable to relatively strong bases. It is also desirable to create a sterically encumbered environment which prevents overalkylations of the protected $N^\beta$ atom of hydrazine unit. In addition, such a protecting group should be easily grafted onto a polymer-support by a reliable chemical transformation.

The reactivity of 5a against various electrophiles such as benzyl bromide, allyl bromide, alkyl iodide, and methyl 2-chloroacetate in the presence of $Cs_2CO_3$ in DMF were tested. In order to determine the degree of overalkylation at the $N^\beta$ position of 5a, a large excess of electrophiles was utilized in all reactions. No overalkylations of 5a were observed in the reactions with electrophiles listed in Table 3-1 even at 50° C. (for the stable electrophiles). On the other hand, the same reactions with BocHNNHBoc gave rise to significant amounts of $N^\alpha,N^\beta$-dialkylsubstituted products.

TABLE 3-1

Alkylations of 5a with representative electrophiles.

| entry | electrophile[1] | temperature (° C.) | time (h)[2] | Product | yield (%)[3] |
|---|---|---|---|---|---|
| 1 | p-ClPhCH$_2$Br | 50 | 12 | 6a[9] | 91 |
| 2 | allyl bromide | 25 | 12 | 6b | 92 |
| 3 | C$_8$H$_{17}$I | 50 | 12 | 6c | 90 |
| 4 | CH$_3$I | 5 | 12 | 6d | 95 |
| 5 | ClCH$_2$CO$_2$Me | 50 | 12 | 6e | 60[4] |

[1]A large excess (10~15 equiv) of electrophile was used.
[2]The reaction was completed within 6 h.
[3]Isolated yield.
[4]The reaction requires a longer time to achieve complete conversion.

Through X-ray analysis of (2,6-dichloro-4-methoxyphenyl)(2,4-dichlorophenyl)methyl acetate and molecular modeling of 5b, the origin of the regioselectivity of alkylations of 5a and stability against bases, acids, and nucleophiles can be attributed to the following reasons. The dihedral angles formed by two planar chlorosubstituted-benzenes and by —CO—O— linkage and the ether methine proton are 83.5° and 159.8°, respectively. It is believed that there is a significant electronic repulsion between the o-chloro atoms in two benzene rings. The o-chloro atom in dichlorobenzene is located towards the carbonyl ester plane. Thus, the chloro atoms at o-positions in two benzenes hinder nucleophilic attacks at the ester carbonyl from both re- and si-faces. The 3,5-dichloro atoms in the anisole moiety attenuate an electron donating character of the methoxy group. Therefore, The urethane 5b exhibits stability against bases, nucleophiles, and acids. To date, the generation of dianion of the hydrazine dicarboxylates under Cs$_2$CO$_3$ in DMF at 50° C. has not been reported. Thus, the observed N$^\alpha$,N$^\beta$-dialkylation of BocHNNHBoc could be explained by a stepwise process. Nevertheless, the generation of anion at the N$^\beta$ position or the approach of electrophiles is hindered or prohibited because of the stereoelectronic factors governed by two planar chlorosubstituted-benzenes.

(2,6-Dichloro-4-hydroxyphenyl)(2,4-dichlorophenyl)methanone, which was obtained in ~70% overall yield by the treatment of the Friedel-Crafts products with saturated HBr in AcOH/water (2:1) followed by washing the crude solid with CHCl$_3$, was converted to the hydroxy-carboxylic acid possessing C6-linker 6 in three steps in 90% overall yield [(1) NaBH$_4$ reduction, (2) alkylation with ethyl 7-bromoheptanoate, and (3) saponification reactions]. The hydroxy-carboxylic acid 6 could be grafted onto the (aminomethyl)polystyrene (~1.2 mmol/g) using a reliable coupling condition [DICI, HOBt, $^i$Pr$_2$NEt/DMF-CH$_2$Cl$_2$ (1/1)]. The resins 7 were then converted to the carbonylimidazole linker which showed good reactivity with hydrazine and monosubstituted hydrazines including BocNHNH$_2$, MeNHNH$_2$, and PhNHNH$_2$ to provide 8a~d whose loading yields were determined to be 0.9~1.2 mmol/g by $^1$H-NMR analyses of the crude materials after cleavage from the resins using 20% TFA in CH$_2$Cl$_2$ for 2 h.

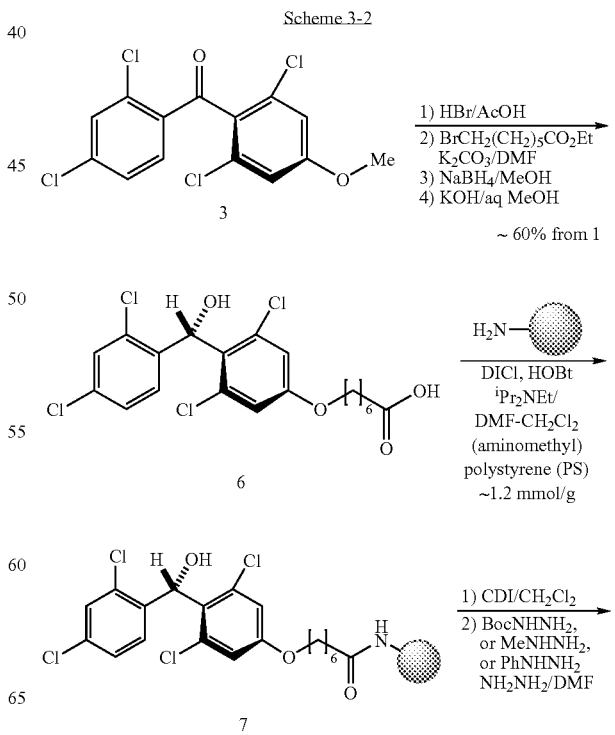

Scheme 3-2

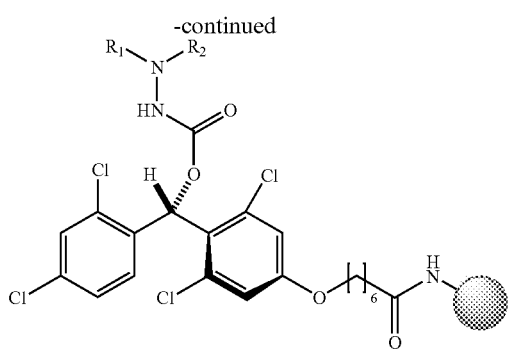

8a: $R_1$ = H, $R_2$ = Boc
8b: $R_1$ = H, $R_2$ = Me
8c: $R_1$ = H, $R_2$ = Ph
8d: $R_1$ = H, $R_2$ = H

8a~d 0.9~1.2 mmol/g

The alkylations observed with 5a in solution were well transferred to the reactions with the resin 8a. As summarized in Table 3-2, the reactions of 8a with the substituted benzyl bromides (10~15 eqiv) in DMF in the presence of $Cs_2CO_3$ (5 equiv) at 50° C. for 12 h gave the corresponding monbenzylated hydrazine.TFA salts 9a~f in good yields, after cleavage from the resins with 20% TFA. Alkylation of 8a with n-octyl iodide followed by cleavage from the resin afforded 1-octylhydrazine.TFA salt (9g) in excellent yield. Allylation of 8a at 50° C. gave 1-allylhydrazine.TFA salt, after cleavage. In these reactions, no overalkylations at the $N^\beta$ position were observed. Similarly, alkylations of 8b and 8c gave the corresponding $N^\alpha,N^\alpha$-dialkylated hydrazine.TFA salts without detectable contamination of by-products in $^1$H-NMR spectra. Symmetrical $N^\alpha,N^\alpha$-dialkylated hydrazine.TFA was also synthesized with the resin 8d with excellent yields. It is worthwhile noting that the solvolytic displacement reactions of 9a~r with TFA provide TFA ester of 7 in near quantitative yield and the alcohol resin 7 can be regenerated by the treatment with aq. $NH_4OH$ in THF-MeOH for 12 h. The regenerated resins could be reused for the synthesis of 9a without noticeable decrease of yield.

TABLE 3-2

High-throughput syntheses of monosubstituted and 1,1-disubstituted hydrazine derivatives.

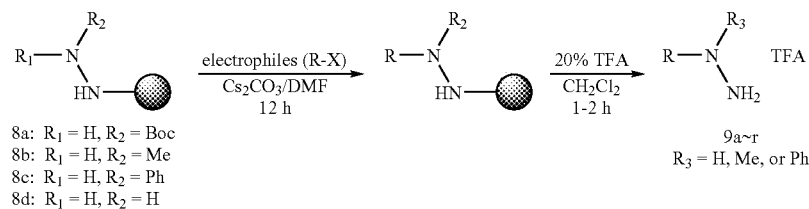

8a: $R_1$ = H, $R_2$ = Boc
8b: $R_1$ = H, $R_2$ = Me
8c: $R_1$ = H, $R_2$ = Ph
8d: $R_1$ = H, $R_2$ = H

9a~r
$R_3$ = H, Me, or Ph

| entry | starting material | electrophile (R) | $R_3$ | product | yield (%)[3] |
|---|---|---|---|---|---|
| 1 | 8a | p-$ClC_6H_4CH_2Br$ | H | 9a | 95 |
| 2 | 8a | p-$CF_3OC_6H_4CH_2Br$ | H | 9b | 93 |
| 3 | 8a | m-$FC_6H_4CH_2Br$ | H | 9c | 95 |
| 4 | 8a | o-$FC_6H_4CH_2Br$ | H | 9d | 92 |
| 5 | 8a | p-$MeSC_6H_4CH_2Br$ | H | 9e | 91 |
| 6 | 8a | allyl bromide | H | 9f | 98 |
| 7 | 8a | $nC_8H_{17}I$ | H | 9g | 92 |
| 8 | 8b | p-$ClC_6H_4CH_2Br$ | Me | 9h | 95 |
| 9 | 8b | p-$CF_3OC_6H_4CH_2Br$ | Me | 9i | 93 |
| 10 | 8b | $nC_8H_{17}I$ | Me | 9j | 92 |
| 11 | 8b | $CH_3I$ | Me | 9k | 98 |
| 12 | 8b | allyl bromide | Me | 9l | 97 |
| 13 | 8c | $nC_8H_{17}I$ | Ph | 9m | 92 |
| 14 | 8c | allyl bromide | Ph | 9n | 95 |
| 15 | 8c | $CH_3I$ | Ph | 9o | 91 |
| 16 | 8d | allyl bromide | allyl | 9p | 94 |
| 17 | 8d | $C_6H_5CH_2Br$ | $C_6H_5CH_2$ | 9q | 94 |
| 18 | 8d | $nC_8H_{17}I$ | $C_8H_{17}$ | 9r | 92 |

[1] A large excess (10~15 equiv) of electrophile and $Cs_2CO_3$ (5 equiv) were used.
[2] The reaction was completed within 6 h.
[3] Isolated yield.
[4] The reaction requires a longer time to achieve complete conversion.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound of the formula:

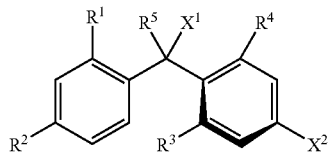

wherein
each of $R^1$, $R^2$, $R^3$, and $R^4$ is independently hydrogen, lower alkyl, or halide, provided at least one of $R^1$, $R^2$, $R^3$, and $R^4$ is halide;
$R^5$ is hydrogen;
each of $X^1$ and $X^2$ is independently —$OR^6$, —$NR^7R^8$, or —$SR^9$;
each $R^6$ is independently hydrogen, alkyl, carbonyl, or a hydroxy protecting group;
each $R^7$ is independently hydrogen or alkyl;
each $R^8$ is independently hydrogen, alkyl, or a nitrogen protecting group; and
each $R^9$ is independently hydrogen, alkyl, or a thiol protecting group.

2. The compound according to claim 1, wherein at least two of $R^1$, $R^2$, $R^3$, and $R^4$ are halides.

3. The compound according to claim 1, wherein at least three of $R^1$, $R^2$, $R^3$, and $R^4$ are halides.

4. The compound according to claim 1, wherein $R^1$, $R^2$, $R^3$, and $R^4$ are halides.

5. The compound according to claim 1, wherein each halide is independently selected from the group consisting of Cl, Br, and I.

6. The compound according to claim 1, wherein halide is Cl.

7. The compound according to claim 1, wherein $X^1$ is —$OR^6$, and $R^6$ is as defined in claim 1.

8. The compound according to claim 7, wherein $R^6$ is hydrogen or carbonyl.

9. The compound according to claim 1, wherein $X^2$ is —$OR^6$, and $R^6$ is as defined in claim 1.

10. The compound according to claim 9, wherein $R^6$ is alkyl.

11. A solid-substrate of the formula:

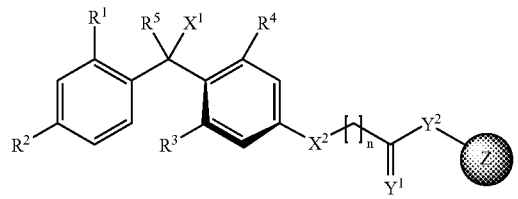

wherein
n is an integer from 1 to about 20;
each of $R^1$, $R^2$, $R^3$, and $R^4$ is independently hydrogen, lower alkyl, or halide, provided at least one of $R^1$, $R^2$, $R^3$, and $R^4$ is halide;
$R^5$ is hydrogen or alkyl;
$X^1$ is —$OR^6$, —$NR^7R^8$, or —$SR^9$;
each of $X^2$ and $Y^2$ is independently —O—, —$NR^8$—, or —S—;
$R^6$ is hydrogen, alkyl, carbonyl, or a hydroxy protecting group;
$R^7$ is hydrogen or alkyl;
each $R^8$ is independently hydrogen, alkyl, or a nitrogen protecting group;
$R^9$ is hydrogen, alkyl, or a thiol protecting group;
$Y^1$ is O, $NR^{10}$, or S;
$R^{10}$ is hydrogen, alkyl, —$OR^{11}$, or —$NR^{12}$;
$R^{11}$ and $R^{12}$ are hydrogen or alkyl; and
Z is a solid substrate.

12. The solid-substrate according to claim 11, wherein $R^1$, $R^2$, $R^3$, and $R^4$ are halides.

13. The solid-substrate according to claim 12, wherein each halide is independently selected from the group consisting of Cl, Br, and I.

14. The solid-substrate according to claim 12, wherein halide is Cl.

15. The solid-substrate according to claim 11, wherein $R^5$ is hydrogen.

16. The solid-substrate according to claim 11, wherein $X^1$ is —$OR^6$, and $R^6$ is that defined in claim 11.

17. The solid-substrate according to claim 16, wherein $R^6$ is hydrogen or carbonyl.

18. The solid-substrate according to claim 11, wherein $X^2$ is —O—.

19. The solid-substrate according to claim 11, wherein $Y^1$ is O.

20. The solid-substrate according to claim 11, wherein $Y^2$ is —$NR^8$—, and $R^8$ is as defined in claim 11.

21. A method of performing solid-phase synthesis comprising
(a) contacting a solid-substrate of the formula:

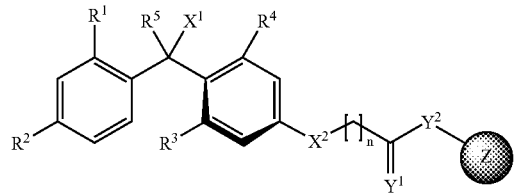

with a first reactive reagent comprising a first corresponding functional group chemically reactive with $X^1$ of the solid-substrate under conditions sufficient to react the corresponding functional group with $X^1$, thus providing a solid-substrate bound product;

(b) optionally reacting the solid-substrate bound product and another reactive reagent comprising another corresponding functional group under conditions sufficient to produce a growing polymeric chain; and (c) repeating said step (b) until a desired product is obtained, wherein n is an integer from 1 to about 20;

each of $R^1$, $R^2$, $R^3$, and $R^4$ is independently hydrogen, lower alkyl, or halide, provided at least one of $R^1$, $R^2$, $R^3$, and $R^4$ is halide;

$R^5$ is hydrogen or alkyl;

$X^1$ is —OH, —$NHR^8$, or —SH;

each of $X^2$ and $Y^2$ is independently —O—, —$NR^8$—, or —S—;

each $R^8$ is independently hydrogen, alkyl, or a nitrogen protecting group;

$Y^1$ is O, $NR^{10}$, or S;

$R^{10}$ is hydrogen, alkyl, —$OR^{11}$, or —$NR^{12}$;

$R^{11}$ and $R^{12}$ are hydrogen or alkyl; and

Z is a solid substrate.

22. The method of claim 21, wherein the reactive reagent is selected from the group consisting of a nucleotide, saccharide, amino acid, and a derivative thereof.

23. The method of claim 21, wherein Z is a bead, wafer, film, disc or plate.

24. The method of claim 23, wherein Z comprises a material selected from organosilane-treated glass, organosilane-treated silicon, polypropylene, polyethylene, and polystyrene.

25. A method for producing a compound of the formula:

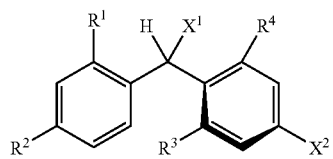

IA said method comprising:

contacting an acyl halide compound of the formula:

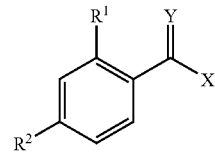

with an aromatic compound of the formula:

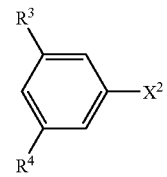

in the presence of a coupling catalyst under conditions sufficient to produce the compound of Formula IA, wherein each of $R^1$, $R^2$, $R^3$, and $R^4$ is independently hydrogen, lower alkyl, or halide, provided at least one of $R^1$, $R^2$, $R^3$, and $R^4$ is halide;

X is a Cl

Y is O;

each of $X^1$ and $X^2$ is independently —$OR^6$, —$NR^7R^8$, or —$SR^9$;

each $R^6$ is independently hydrogen, alkyl, carbonyl, or a hydroxy protecting group;

each $R^7$ is independently hydrogen or alkyl;

each $R^8$ is independently hydrogen, alkyl, or a nitrogen protecting group; and each $R^9$ is independently hydrogen, alkyl, or a thiol protecting group.

* * * * *